United States Patent
Kondo et al.

(10) Patent No.: US 6,579,577 B2
(45) Date of Patent: Jun. 17, 2003

(54) SUBSTITUTED BENZENE DERIVATIVE, LIQUID CRYSTAL COMPOSITION, AND LIQUID CRYSTAL DISPLAY ELEMENT

(75) Inventors: Tomoyuki Kondo, Ichihara (JP); Shuichi Matsui, Ichihara (JP); Kazutoshi Miyazawa, Yachiyo (JP); Hiroyuki Takeuchi, Ichihara (JP); Yasuhiro Kubo, Ichihara (JP); Fusayuki Takeshita, Sodegaura (JP); Etsuo Nakagawa, Ichihara (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/917,271

(22) Filed: Jul. 30, 2001

(65) Prior Publication Data

US 2002/0166994 A1 Nov. 14, 2002

Related U.S. Application Data

(63) Continuation-in-part of application No. 09/242,811, filed as application No. PCT/JP97/03403 on Sep. 25, 1997, now abandoned.

(30) Foreign Application Priority Data

Sep. 25, 1996 (JP) ............................................. 8-272857

(51) Int. Cl.[7] .................. C09K 19/12; C09K 19/52; C07C 25/13
(52) U.S. Cl. ............. 428/1.1; 252/299.01; 252/299.66; 570/127; 570/129; 570/184
(58) Field of Search ..................... 252/299.66, 299.01; 428/1.1; 570/127, 129, 184

(56) References Cited

U.S. PATENT DOCUMENTS

| 5,308,542 A | 5/1994 | Poetsch et al. |
| 5,496,499 A | 3/1996 | Poetsch et al. |
| 5,637,257 A | 6/1997 | Coates et al. |
| 5,641,429 A | 6/1997 | Reiffenrath et al. |
| 5,730,904 A | 3/1998 | Bartmann et al. |
| 5,746,938 A | 5/1998 | Coates et al. |
| 5,753,142 A | 5/1998 | Plach et al. |
| 5,874,022 A | 2/1999 | Kubo et al. |
| 5,932,138 A | 8/1999 | Plach et al. |
| 6,004,479 A | 12/1999 | Weber et al. |

FOREIGN PATENT DOCUMENTS

| DE | 4101543 | 8/1991 |
| JP | 2-67232 | 3/1990 |
| JP | 2-233626 | 9/1990 |
| JP | 6-49448 | 2/1994 |
| JP | 6-504032 | 5/1994 |
| JP | 6-263691 | 9/1994 |
| WO | WO 90/08757 | 8/1990 |
| WO | WO 91/03450 | 3/1991 |
| WO | WO 91/08184 | 6/1991 |

*Primary Examiner*—Shean C. Wu
(74) *Attorney, Agent, or Firm*—McDermott, Will & Emery

(57) ABSTRACT

There is provided a liquid crystalline compound having a high voltage holding ratio which has a very small degree of temperature dependence, a low threshold voltage which has a very small degree of temperature dependence, a high Δn, and excellent miscibility with other liquid crystal materials at low temperature; a liquid crystal composition; and a liquid crystal display element, and the liquid crystalline compound is a substituted benzene derivative represented by general formula (1), (1)

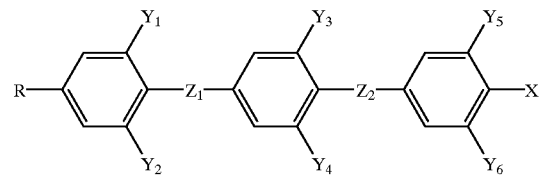

where, R represents a straight chain or branched alkyl group having 1 to 20 carbon atoms in which each of optional and nonadjacent methylene groups (—$CH_2$—) may be substituted by an oxygen atom; X represents a halogen atom, —$CF_3$, —$CF_2H$, —$CFH_2$, —$OCF_3$ or —$OCF_2H$; each of $Z_1$ and $Z_2$ independently represents —$(CH_2)_2$—, —$(CH_2)_4$—, —$CH_2O$—, —$OCH_2$— or a covalent bond, but $Z_1$ and $Z_2$ are not covalent bonds simultaneously; each of $Y_1$, $Y_2$, $Y_3$, $Y_4$, $Y_5$, and $Y_6$ independently represents H or F, but at least one of $Y_1$, $Y_2$, $Y_3$, and $Y_4$ represents F.

13 Claims, No Drawings

SUBSTITUTED BENZENE DERIVATIVE, LIQUID CRYSTAL COMPOSITION, AND LIQUID CRYSTAL DISPLAY ELEMENT

REFERENCE TO RELATED APPLICATION

This Application is a continuation-in-part of application Ser. No. 09/242,811, filed Feb. 24, 1999, now abandoned, which is a 371 of International Application No. PCT/JP97/03403, whose international filing date is Sep. 25, 1997, which in turn claims the benefit of Japanese Patent Application No. 272857/1996, filed Sep. 25, 1996, the disclosures of which Applications are incorporated by reference herein. The benefit of the filing and priority dates of the International and Japanese Applications is respectfully requested.

TECHNICAL FIELD

The present invention relates to a novel liquid crystalline compound and a liquid crystal composition. In particular, the present invention relates to a compound having fluorine-substituted 1,4-phenylene groups, a liquid crystal composition containing such a compound, and a liquid crystal display element constituted from such a liquid crystal composition.

BACKGROUND ART

Display elements produced from liquid crystalline compounds have been used widely in displays for watches and clocks, electronic calculators, word processors, and the like. (The term "liquid crystalline compound"0 used herein is a generic designation for compounds that exhibit a liquid crystal phase, as well as compounds that do not exhibit a liquid crystal phase but are useful as constituting components for liquid crystal compositions.) In recent years, TFT displays having characteristics such as high contrast and wide viewing angle have been actively studied.

For liquid crystal compositions for TFT displays, there are demanded such properties as a high voltage holding ratio which has a very small degree of temperature dependence, a low threshold voltage (Vth) which has a very small degree of temperature dependence, wide range of mesophase, excellent miscibility with other liquid crystal materials, and low viscosity. Further demanded are improved response speed and contrast when they are used as a constitutional component of liquid crystal components. For example, compositions having a high Δn or a low threshold voltage is useful for improving response speed.

Fluorine-substituted liquid crystalline compounds are suitable as components constituting liquid crystal compositions having such properties, and a large number of such compounds have been examined as described in (1) Japanese Patent Publication No. 63-13411, (2) Japanese Patent Publication No. 63-44132, (3) Japanese Patent Application Laid Open No. 2-233626, (4) Japanese-translated PCT Patent Application Laid-open No. 2-501311, (5) Japanese-translated PCT Patent Application Laid-open No. 3-500413, (6) Japanese-translated PCT Patent Application Laid-open No. 3-503771, (7) Japanese-translated PCT Patent Application Laid-open No. 3-504018, (8) Japanese Patent Application Laid Open No. 4-217930, (9) Japanese-translated PCT Patent Application Laid-open No. 4-501575, (10) Japanese-translated PCT-Patent Application Laid-open No. 5-502676, (11) Japanese-translated PCT Patent Application Laid-open No. 6-504032, and (12) EP 436089.

DISCLOSURE OF INVENTION

An object of the present invention is to provide a liquid crystalline compound having a high voltage holding ratio which has a very small degree of temperature dependence, a low threshold voltage which has a very small degree of temperature dependence, a high Δn, and excellent miscibility with other liquid crystal materials at low temperature; liquid crystal compositions produced from these compounds having especially improved response speed and contrast; and liquid crystal display elements constituted from such liquid crystal compositions. The present inventors found that the above object is achieved by substituted benzene derivatives represented by general formula (1), thus completing the present invention.

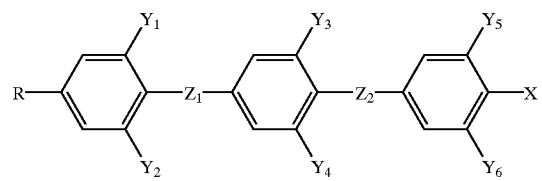

(1)

where, R represents a straight chain or branched alkyl group having 1 to 20 carbon atoms, in which each of optional and nonadjacent methylene groups (—$CH_2$—) may be substituted by an oxygen atom; X represents a halogen atom, —$CF_3$, —$CF_2H$, —$CFH_2$, —$OCF_3$ or —$OCF_2H$; each of $Z_1$ and $Z_2$ independently represents —$(CH_2)_2$—, —$(CH_2)_4$—, —$CH_2O$—, —$OCH_2$— or a covalent bond, but $Z_1$ and $Z_2$ are not covalent bonds simultaneously; each of $Y_1$, $Y_2$, $Y_3$, $Y_4$, $Y_5$ and $Y_6$ independently represents H or F, but at least one of $Y_1$, $Y_2$, $Y_3$ and $Y_4$ represents F; and, 1) when $Z_1$=—$(CH_2)_2$—, $Z_2$=a covalent bond, and
   a) when $Y_1$=F and $Y_2$=$Y_3$=$Y_4$=H, $Y_5$=F,
   b) when $Y_3$=F and $Y_1$=$Y_2$=$Y_4$=H, $Y_5$=$Y_6$=F,
   c) when $Y_1$=$Y_2$=F, $Y_3$=$Y_4$=H and X=F or —$CF_3$, $Y_5$=F,
   d) when $Y_1$=$Y_2$=F, $Y_3$=$Y_4$=H and X=—$CF_2H$, $Y_6$=H,
   e) when $Y_1$=$Y_3$=F and $Y_2$=$Y_4$=H, $Y_5$=$Y_6$=F or $Y_5$=$Y_6$=H,
   f) when $Y_3$=$Y_4$=F, $Y_1$=$Y_2$=H and X=—$OCF_3$ or —$OCF_2H$, $Y_5$=F,
   g) when $Y_3$=$Y_4$=F, 1=$Y_2$=H and X=—$CF_3$ or —$CF_2H$, $Y_5$=$Y_6$=F,
   h) when $Y_1$=$Y_2$=$Y_3$=F, $Y_4$=H and X=F, —$OCF_3$, —$OCF_2H$, —$CF_3$ or —$CF_2H$, $Y_6$=H,
   i) when $Y_1$=$Y_2$=$Y_3$=F, $Y_4$=H and X=Cl, $Y_5$=F,
   j) when $Y_1$=$Y_3$=$Y_4$=F, $Y_2$=H and X=F, $Y_6$=F,
   k) when $Y_1$=$Y_2$=$Y_3$=$Y_4$=F and X=F, —$OCF_3$, —$OCF_2H$, —$CF_3$ or —$CF_2H$, $Y_6$=H, and
   l) when $Y_1$=$Y_2$=$Y_3$=$Y_4$=F and X=Cl, $Y_5$=F, 2) when $Z_1$=a covalent bond, $Z_2$=—$(CH_2)_2$—, and
   m) when $Y_1$=F and $Y_2$=$Y_3$=$Y_4$ H, $Y_5$=F and $Y_6$=H,
   n) when $Y_3$=F and $Y_1$=$Y_2$=$Y_4$=H, $Y_5$=$Y_6$=F or $Y_5$=$Y_6$=H,
   o) when $Y_1$=$Y_3$=F and $Y_2$=$Y_4$=H, $Y_5$=$Y_6$=F or $Y_5$=$Y_6$=H,
   p) when $Y_3$=$Y_4$=F, $Y_1$=$Y_2$=H and X=F, Cl, —$OCF_3$, —$OCF_2H$ or —$CF_2H$, $Y_6$=H,
   q) when $Y_1$=$Y_3$=$Y_4$=F and $Y_2$=H, $Y_6$=H,
   r) when $Y_1$=$Y_2$=$Y_3$=$Y_4$=F, $Y_6$=H, with the proviso that when $Z_1$=—$(CH_2)_2$—, $Z_2$=a covalent bond, $Y_3$=$Y_4$=F and $Y_1$=$Y_2$=H, X is neither F nor Cl; when $Z_1$ is a covalent bond, $Z_2$ is —$(CH_2)_2$—, $Y_1$=F and $Y_2$=$Y_3$=$Y_4$ H, X is neither F, Cl nor $CF_3$; and any atom constituting this compound may be substituted by an isomer thereof.

Although some of the compounds represented by general formula (1) disclosed herein are included only perfunctorily in the above references (6) through (12) and other references, these references provide neither data on the compounds of the present invention nor specific descriptions of properties thereof, nor do they suggest the present invention.

Compounds represented by general formula (1) are classified into the following (a-1) through (a-32), and (b-1) through (b-32):

| | |
|---|---|
| R—B(F)—(CH$_2$)$_2$—B—Q | (a-1) |
| R—B—(CH$_2$)$_2$—B(F)—Q | (a-2) |
| R—B(F,F)—(CH$_2$)$_2$—B—Q | (a-3) |
| R—B(F)—(CH$_2$)$_2$—B(F)—Q | (a-4) |
| R—B—(CH$_2$)$_2$—B(F,F)—Q | (a-5) |
| R—B(F,F)—(CH$_2$)$_2$—B(F)—Q | (a-6) |
| R—B(F)—(CH$_2$)$_2$—B(F,F)—Q | (a-7) |
| R—B(F,F)—(CH$_2$)$_2$—B(F,F)—Q | (a-8) |
| R—B(F)—(CH$_2$)$_4$—B—Q | (a-9) |
| R—B—(CH$_2$)$_4$—B(F)—Q | (a-10) |
| R—B(F,F)—(CH$_2$)$_4$—B—Q | (a-11) |
| R—B(F)—(CH$_2$)$_4$—B(F)—Q | (a-12) |
| R—B—(CH$_2$)$_4$—B(F,F)—Q | (a-13) |
| R—B(F,F)—(CH$_2$)$_4$—B(F)—Q | (a-14) |
| R—B(F)—(CH$_2$)4—B(F,F)—Q | (a-15) |
| R—B(F,F)—(CH$_2$)$_4$—B(F,F)—Q | (a-16) |
| R—B(F)—CH$_2$O—B—Q | (a-17) |
| R—B—CH$_2$O—B(F)—Q | (a-18) |
| R—B(F,F)—CH$_2$O—B—Q | (a-19) |
| R—B(F)—CH$_2$O—B(F)—Q | (a-20) |
| R—B—CH$_2$O—B(F,F)—Q | (a-21) |
| R—B(F,F)—CH$_2$O—B(F)—Q | (a-22) |
| R—B(F)—CH$_2$O—(F,F)—Q | (a-23) |
| R—B(F,F)—CH$_2$O—B(F,F)—Q | (a-24) |
| R—B(F)—OCH$_2$—B—Q | (a-25) |
| R—B—OCH$_2$—B(F)—Q | (a-26) |
| R—B(F,F)—OCH$_2$—B—Q | (a-27) |
| R—B(F)—OCH$_2$—B(F)—Q | (a-28) |
| R—B—OCH$_2$—B(F,F)—Q | (a-29) |
| R—B(F,F)—OCH$_2$—B(F)—Q | (a-30) |
| R—B(F)—OCH$_2$—B(F,F)—Q | (a-31) |
| R—B(F,F)—OCH$_2$—B(F,F)—Q | (a-32) |
| R—B(F)—B—(CH$_2$)$_2$—Q | (b-1) |
| R—B—B(F)—(CH$_2$)$_2$—Q | (b-2) |
| R—B(F,F)—B—(CH$_2$)$_2$—Q | (b-3) |
| R—B(F)—B(F)—(CH$_2$)$_2$—Q | (b-4) |
| R—B—B(F,F)—(CH$_2$)$_2$—Q | (b-5) |
| R—B(F,F)—B(F)—(CH$_2$)$_2$—Q | (b-6) |
| R—B(F)—B(F,F)—(CH$_2$)$_2$—Q | (b-7) |
| R—B(F,F)—B(F,F)—(CH$_2$)$_2$—Q | (b-8) |
| R—B(F)—B—(CH$_2$)$_4$—Q | (b-9) |
| R—B—B(F)—(CH$_2$)$_4$—Q | (b-10) |
| R—B(F,F)—B—(CH$_2$)$_4$—Q | (b-11) |
| R—B(F)—B(F)—(CH$_2$)$_4$—Q | (b-12) |
| R—B—B(F,F)—(CH$_2$)$_4$—Q | (b-13) |
| R—B(F,F)—B(F)—(CH$_2$)$_4$—Q | (b-14) |
| R—B(F)—B(F,F)—(CH$_2$)$_4$—Q | (b-15) |
| R—B(F,F)—B(F,F)—(CH$_2$)$_4$—Q | (b-16) |
| R—B(F)—B—CH$_2$O—Q | (b-17) |
| R—B—B(F)—CH$_2$O—Q | (b-18) |
| R—B(F,F)—B—CH$_2$O—Q | (b-19) |
| R—B(F)—B(F)—CH$_2$O—Q | (b-20) |
| R—B—B(F,F)—CH$_2$O—Q | (b-21) |
| R—B(F,F)—B(F)—CH$_2$O—Q | (b-22) |
| R—B(F)—B(F,F)—CH$_2$O—Q | (b-23) |
| R—B(F,F)—B(F,F)—CH$_2$O—Q | (b-24) |
| R—B(F)—B—OCH$_2$—Q | (b-25) |
| R—B—B(F)—OCH$_2$—Q | (b-26) |
| R—B(F,F)—B—OCH$_2$—Q | (b-27) |
| R—B(F)—B(F)—OCH$_2$—Q | (b-28) |
| R—B—B(F,F)—OCH$_2$—Q | (b-29) |
| R—B(F,F)—B(F)—OCH$_2$—Q | (b-30) |
| R—B(F)—B(F,F)—OCH$_2$—Q | (b-31) |
| R—B(F,F)—B(F,F)—OCH$_2$—Q | (b-32) |

In these formulas, R has the same meaning as described above; B represents a 1,4-phenylene group; B(F) represents a 3-fluoro-1,4-phenylene group; B(F,F) represents a 3,5-difluoro-1,4-phenylene group; and Q represents the group shown below.

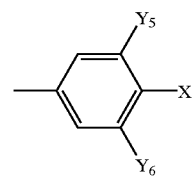

Where $Y_5$, $Y_6$, and X have the same meanings as described above.

Although compounds represented by the above formulas (a-1) through (a-32), and (b-1) through (b-32) are all preferred, compounds represented by formulas (a-1) through (a-8), (a-17) through (a-24), (b-1) through (b-8), and (b--17) through (b-24) are particularly preferred.

In these formulas, R represents a straight-chain or branched alkyl group having 1 to 20 carbon atoms specifically exemplified by methyl, ethyl, propyl, butyl, pentyl, hexyl, heptyl, decyl, pentadecyl, and icosyl groups as a straight-chain alkyl group; and isopropyl, sec-butyl, tert-butyl, 2-methyl-butyl, isopentyl, isohexyl, 3-ethyloctyl, 3,8-dimethyltetradecyl, and 5-ethyl-5-methylnonadecyl groups as a branched alkyl group. The branched alkyl group may be the one having optical activity, and such a group is useful as a chiral doping agent.

Each of optional, nonadjacent methylene groups may be substituted by an oxygen atom, specifically exemplified by an alkoxyl group such as methoxy, ethoxy, propoxy, butoxy, pentyloxy, and nonyloxy groups; and an alkoxyalkyl group such as methoxymethyl, methoxyethyl, methoxypropyl, methoxybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, hexyloxypropyl, heptyloxymethyl, and octyloxymethyl groups.

In general formula (1), each of $Z_1$ and $Z_2$ independently represents —(CH$_2$)$_2$—, —(CH$_2$)$_4$—, —CH$_2$O—, —OCH$_2$—, or a covalent bond, and preferably, one of $Z_1$ and $Z_2$ is a covalent bond, and more preferably, one of $Z_1$ and $Z_2$ is a covalent bond and the other is —(CH$_2$)$_2$—, —CH$_2$O—, or —OCH$_2$—.

Any atom constituting the compound represented by formula (1) may be substituted by an isomer thereof.

By suitable selection of these substituents or bonding groups, a compound having desired properties can be obtained.

A liquid crystalline compound according to the present invention represented by general formula (1) can be produced through commonly employed organic synthesis methods. For example, such a compound can be produced easily by the following method:

scheme 1

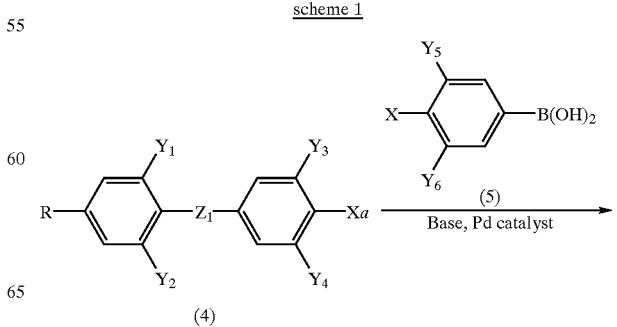

(4)

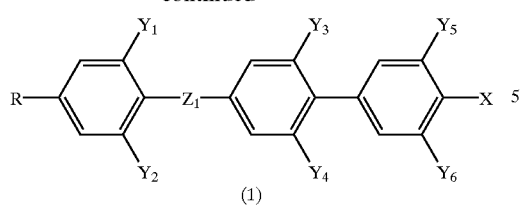

(1)

scheme 2

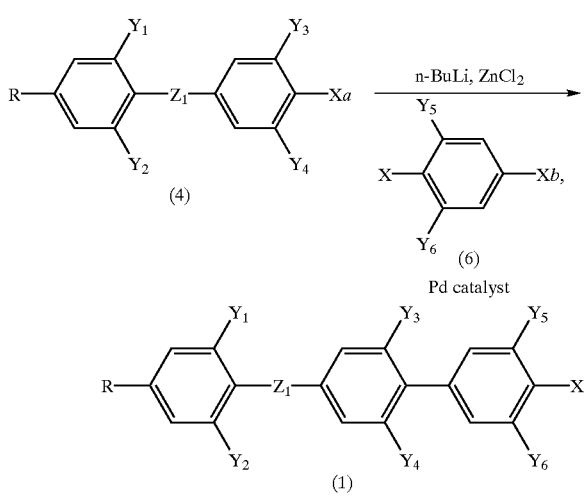

scheme 3

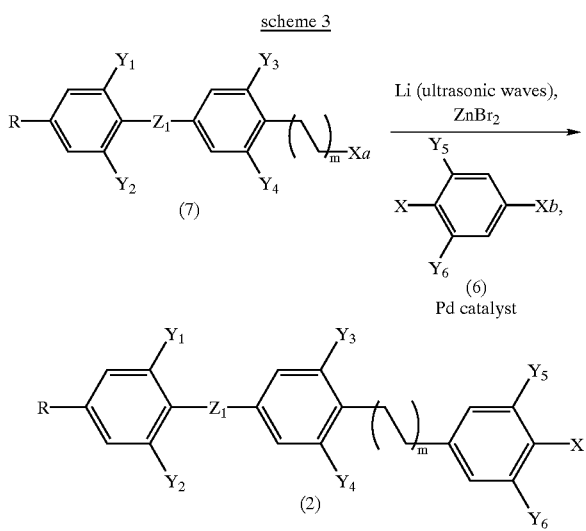

scheme 4

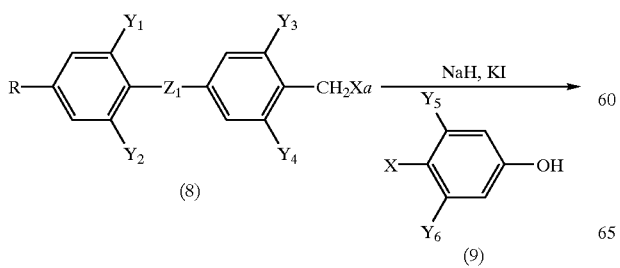

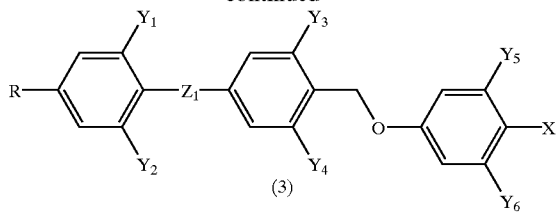

(3)

where R, X, $Y_1$ to $Y_6$, and $Z_1$ have the same meanings as described above; each of Xa and Xb represents a halogen atom; and m represents 1 or 2.

As is shown in Scheme 1, compound (1) of the present invention can be produced by allowing a halogen compound (4) to react with a dihydroxyborane derivative (5) in a mixed solvent containing toluene or xylene, an alcohol such as ethanol, and water, in the presence of a base such as $K_2CO_3$ or $Na_2CO_3$ and a catalyst such as palladium supported by graphite carbon (Pd—C), $Pd(PPh_3)_4$, or $PdCl_2(PPh_3)_2$. Alternatively, as Scheme 2 shows, compound (1) of the present invention can be produced by allowing a halogen compound (4) to react with a lithium compound such as n-BuLi and a zinc compound such as $ZnCl_2$ or $ZnBr_2$, and then with a halogen compound (6).

As Scheme 3 shows, the compound (2) of the present invention can be produced by allowing a halogen compound (7) to react with lithium, then with a zinc compound and a halogen compound (6).

Also, as Scheme 4 shows, the compound (3) of the present invention can be produced by allowing a halogen compound (8) to react with a phenol derivative (9) in a solvent such as dimethyl sulphoxide, dimethyl formamide (DMF), 1,2-dimethoxyethane, tetrahydrofuran, hexamethylphosphorous triamide, or toluene, in the presence of a base such as sodium amide (J. B. Wright, et al., Journal of the American Chemical Society, 70, 3098(1948)), potassium carbonate (W. T. Olson, et al., Journal of the American Chemical Society, 69, 2451(1947)), triethyl amine (R. L. Merker, et al., the Journal of Organic Chemistry, 26, 5180(1961)), sodium hydroxide (C. Wilkins, Synthesis, 1973, 156), potassium hydroxide (J. Rebek, et al., the Journal of Organic Chemistry, 44, 1485 (1979)), barium hydroxide (Kawabe, et al., the Journal of Organic Chemistry, 37, 4210(1972)), or sodium hydride (C. J. Stark, Tetrahedron Letters, 22, 2089, (1981), and K. Takai, et al., Tetrahedron Letters, 21, 1657, (1980)).

In general formula (1), a compound containing —O— in R can also be produced by similar methods.

The substituent X can be easily introduced by use of a previously introduced material, or through a well-known reaction at any process stage. Specific examples are shown below. In the formulas, Rx represents the following group:

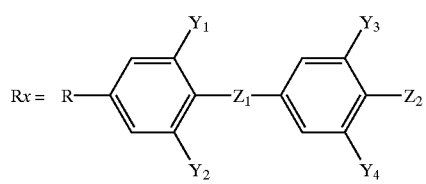

where R, $Y_1$ to $Y_4$, $Z_1$, and $Z_2$ have the same meanings as described above.

scheme 5

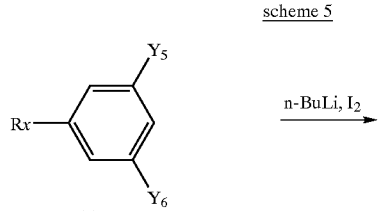

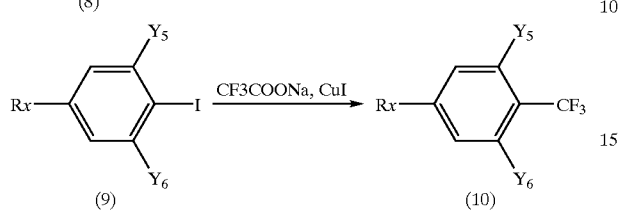

scheme 6

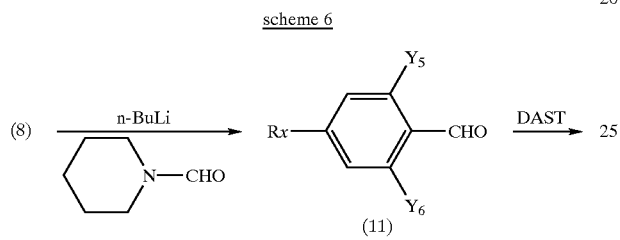

scheme 7

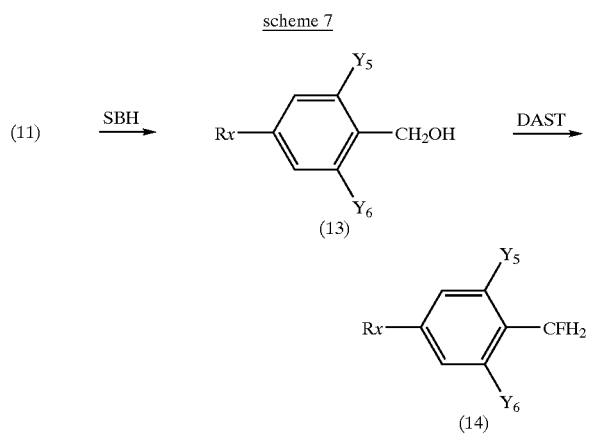

scheme 8

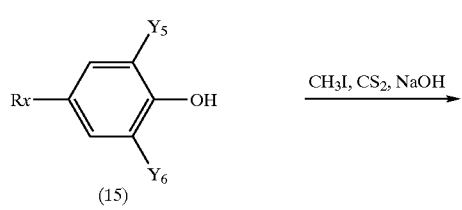

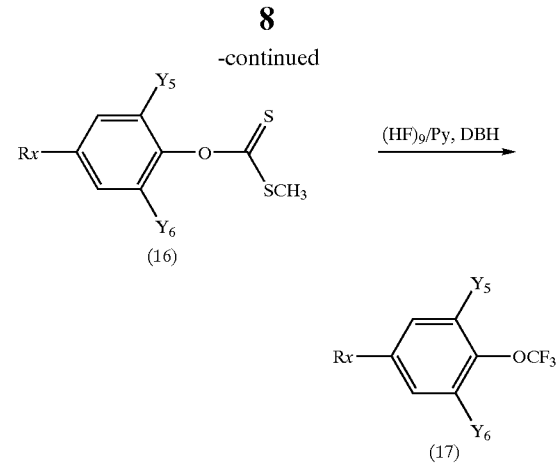

scheme 9

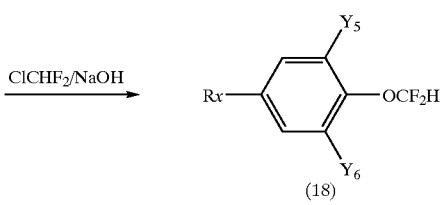

where $Y_5$ and $Y_6$ have the same meanings as described above.

As Scheme 5 shows, a trifluoromethyl compound (10) can be produced by allowing compound (8) to react with a lithium compound such as n-butyl lithium and iodine to form compound (9), and allowing compound (9) to react with sodium trifluoroacetate/copper(I) iodide (G. E. Carr, et al., Journal of the Chemical Society Parkin Transactions I, 921, (1988)), or methyl fluorosulfonyl difluoroacetate/copper(I) iodide (Q. Y. Chen, et al., Journal of the Chemical Society Chemical Communications, 705 (1989)).

As Scheme 6 shows, a difluoromethyl compound (12) can be produced by allowing compound (8) to react with a lithium compound such as n-butyl lithium and a formylating agent such as N-formyl piperidine (G. A. Olah, et al., Angewandte Chemie International Edition in English, 20, 878(1981)), N-formyl morpholine (G. A. Olah, et al., the Journal of Organic Chemistry, 49, 385(1984)), or DMF (G. Boss, et al., Chemische Berichte, 1199(1989)) to form compound (11), and allowing compound (11) to react with a fluorinating agent such as diethylaminosulfur trifluoride (DAST) (W. J. Middleton, et al., the Journal of Organic Chemistry, 40, 574(1975); S. Rozen, et al., Tetrahedron Letters, 41, 111(1985); M.Hudlicky, Organic Reactions, 35, 513(1988); and P. A. Messina, et al., the Journal of Fluorine Chemistry, 42, 137(1989)), or morpholinosulfur trifluoride (K. C. Mange, et al., the Journal of Fluorine Chemistry, 43, 405(1989)).

As Scheme 7 shows, a monofluoromethyl compound (14) can be produced by reducing compound (11) with a reductant such as sodium borohydride (SBH), lithium aluminum hydride (LAH), diisobutyl aluminum hydride (DIBAL), or sodium bis-(2-methoxyethoxy)-aluminum hydride (SBMEA) to form compound (13), and allowing compound (13) to react with a fluorinating agent such as DAST.

As Scheme 8 shows, a trifluoromethoxy compound (17) can be produced by converting compound (15) by use of the method of Albert, et al. (Synthetic Communications, 19, 547(1989)) to form compound (16), and fluorinating compound (16) through the method of Kuroboshi, et al. (Tetrahedron Letters, 33, 29, 4173(1992)).

As Scheme 9 shows, a difluoromethoxy compound (18) can be produced by fluorinating compound (15) in a chlorodifluoromethane/sodium hydroxide system (Japanese-translated PCT Patent Application Laid-open No. 3-500413). Alternatively, it can be produced by use of the method of Chen, et al. (the Journal of Fluorine Chemistry, 44, 433(1989).

Halogen compounds and dihydroxyborane derivatives used as the materials can be produced by general organic synthesis methods, such as the following schemes:

scheme 10

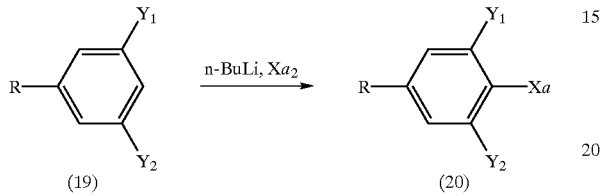

scheme 11

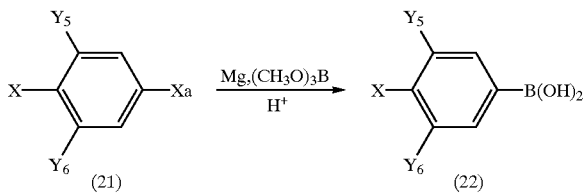

Where, R, X, Xa, $Y_1$, $Y_2$, $Y_5$, and $Y_6$ have the same meanings as described above.

As Scheme 10 shows, a halogen compound (20) can be produced by allowing compound (19) to react with a lithium compound such as n-BuLi, and iodine or bromine.

Also, as Scheme 11 shows, a dihydroxyborane derivative (22) can be produced by allowing compound (21) to react with a Grignard reagent prepared from and magnesium and a borane derivative such as trimethoxyborane or triisopropyloxyborane, and hydrolyzing the reaction product with hydrochloric acid or the like.

The reactions described above are well known to the art, and, needless to say, other known reactions may also be used.

Liquid crystalline compounds of the present invention thus obtained have a high voltage holding ratio which has a very small degree of temperature dependence, a low threshold voltage which has a very small degree of temperature dependence, and a high Δn. In addition, these compounds are easily mixed with various liquid crystal materials, and have high solubility even at low temperature.

Also, the liquid crystalline compounds of the-present invention are physically and chemically stable under conditions where liquid crystal display elements are normally used, and are excellent materials for the components of nematic liquid crystal compositions.

The compounds of the present invention can also be suitably used as the components of liquid compositions for TN, STN, and TFT displays.

The liquid crystal composition of the present invention will be described in detail below. Preferably, the liquid crystal composition according to the present invention contains at least one of the compounds represented by general formula (1) in a quantity of 0.1 to 99.9% by weight.

Specifically, liquid crystal compositions provided by the present invention are produced by mixing the first component containing at least one of the compounds represented by general formula (1), with a compound selected from a group of compounds represented by the following general formulas (2) to (9), depending on the application of the liquid crystal composition.

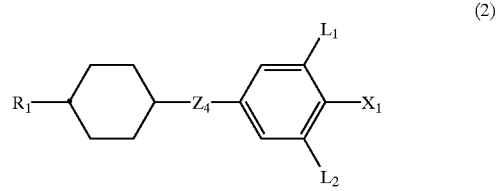

(2)

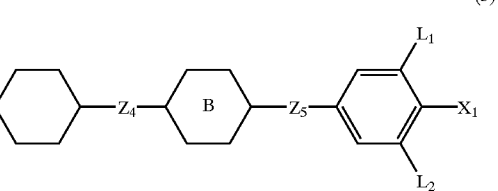

(3)

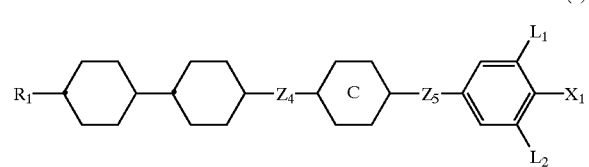

(4)

where, each of $R_4$ and $R_5$ independently represents an alkyl group having 1 to 10 carbon atoms in which each of optional and nonadjacent methylene groups may be substituted by an oxygen atom or —CH=CH—, and optional hydrogen atoms may be substituted by fluorine atoms; each of ring G, ring I and ring J independently represents trans-1,4-cyclohexylene, pyrimidine-2,5-diyl, or 1,4-phenylene in which hydrogen atoms may be substituted by fluorine atoms; each of $Z_7$ and $Z_8$ independently represents —C≡C—, —COO—, —CH$_2$CH$_2$—, —CH=CH— or a covalent bond.

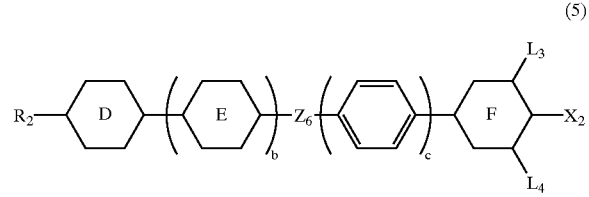

(5)

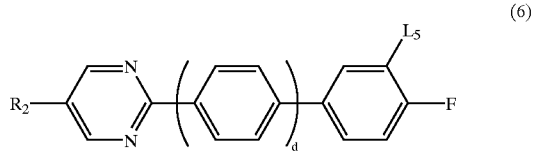

(6)

where, each of $R_2$ and $R_3$ independently represents an alkyl group having 1 to 10 carbon atoms in which each of optional and nonadjacent methylene groups may be substituted by an oxygen atom or —CH=CH—, and optional hydrogen atoms may be substituted by fluorine atoms; $X_2$ represents a CN group or —C≡C—CN; ring D represents trans-1,4-cyclohexylene, 1,4-phenylene, 1,3-dioxane-2,5-diyl or pyrimidine-2,5-diyl; ring E represents trans-1,4-cyclohexylene, 1,4-phenylene in which hydrogen atoms may be substituted by fluorine atoms or pyrimidine-2,5-diyl; ring F represents trans-1,4-cyclohexylene or 1,4-phenylene; $Z_6$ represents a 1,2-ethylene group, —COO— or a covalent bond; each of $L_3$, $L_4$, and $L_5$ independently represents a hydrogen atom or a fluorine atom; each of b, c and d independently represents 0 or 1.

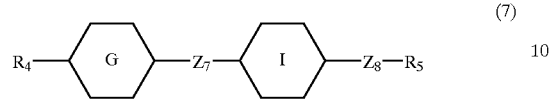
(7)

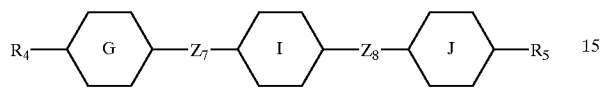
(8)

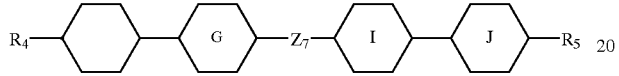
(9)

where, each of $R_4$ and $R_5$ independently represents an alkyl group having 1 to 10 carbon atoms in which each of optional and nonadjacent methylene groups may be substituted by an oxygen atom or —CH=CH—, and optional hydrogen atoms may be substituted by fluorine atoms; each of ring G, ring I and ring J independently represents trans-1,4-cyclohexylene, pyrimidine-2,5-diyl, or 1,4-phenylene in which hydrogen atoms may be substituted by fluorine atoms; each of $Z_7$ and $Z_8$ independently represents —C≡C—, —COO—, —CH$_2$CH$_2$—, —CH=CH— or a covalent bond.

Preferred examples of compounds represented by general formulas (2) to (4) used in the liquid crystal composition of the present invention are as follows:

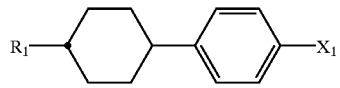
(2-1)

(2-2)

(2-3)

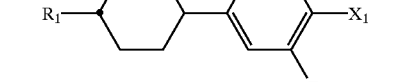
(2-4)

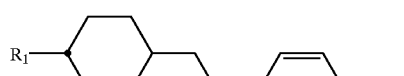
(2-5)

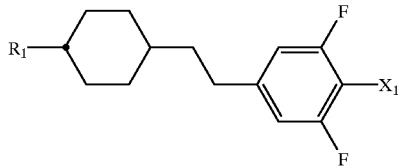
(2-6)

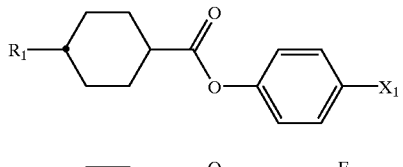
(2-7)

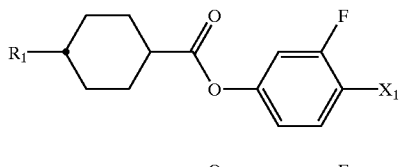
(2-8)

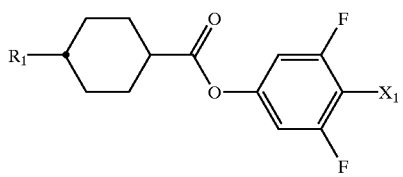
(2-9)

(3-1)

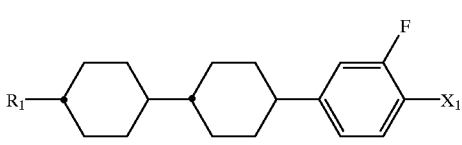
(3-2)

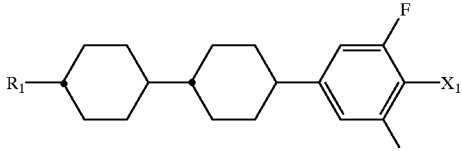
(3-3)

(3-4)

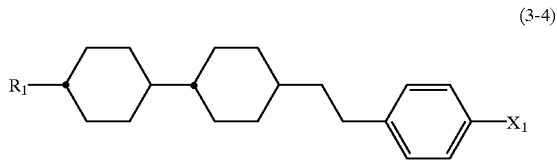

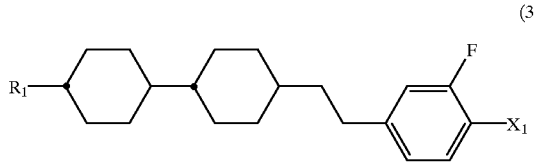
(3-5)

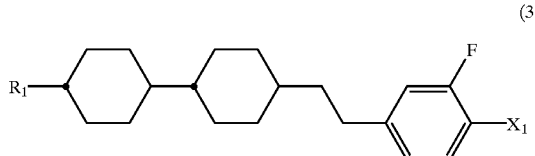
(3-6)

-continued
(3-7)
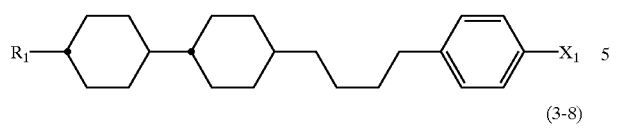
(3-8)
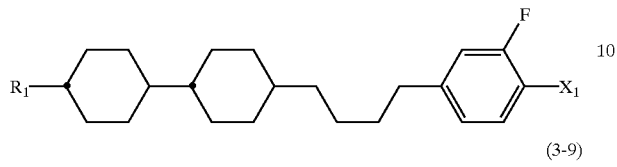
(3-9)
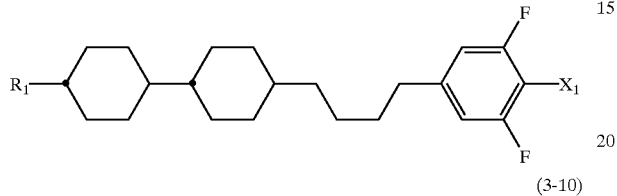
(3-10)
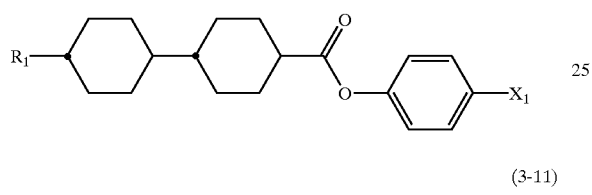
(3-11)
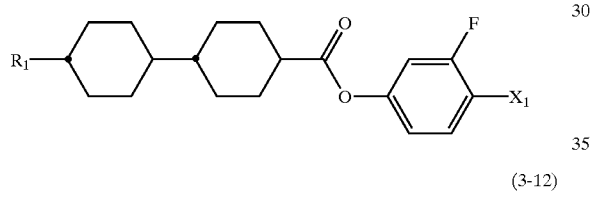
(3-12)
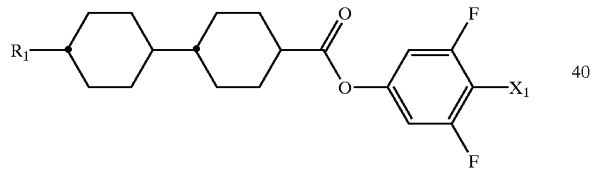
(3-13)
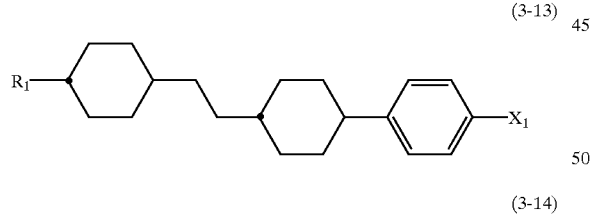
(3-14)
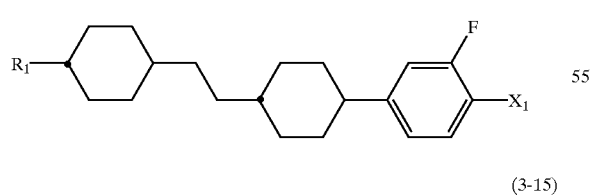
(3-15)
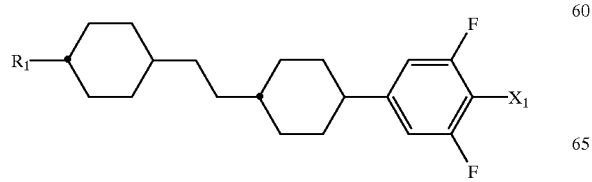
(3-16)
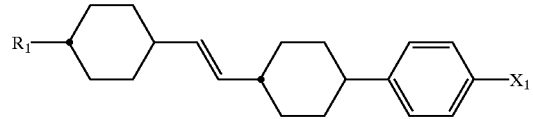
(3-17)
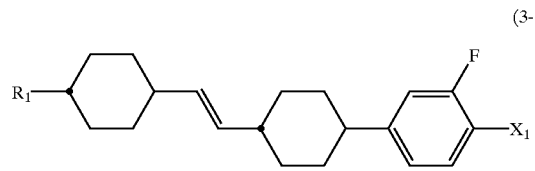
(3-18)
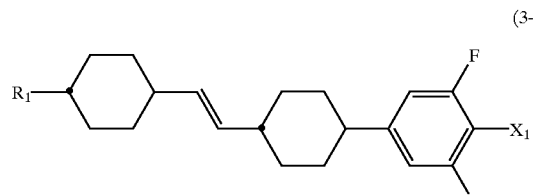
(3-19)
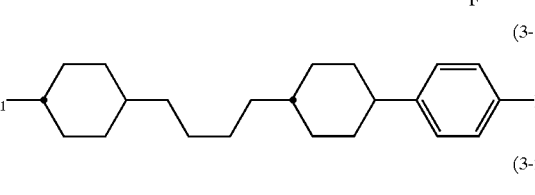
(3-20)
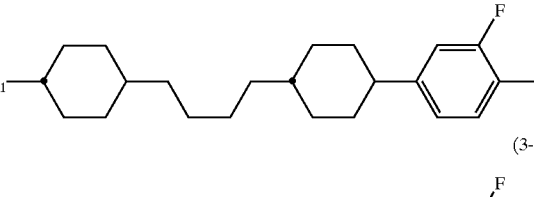
(3-21)
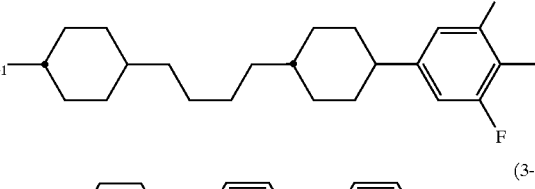
(3-22)
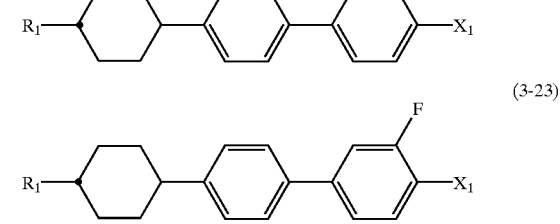
(3-23)
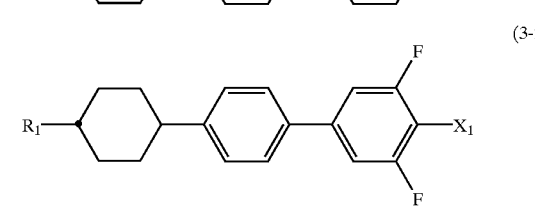
(3-24)
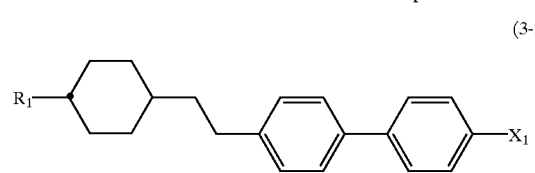
(3-25)

(3-26)
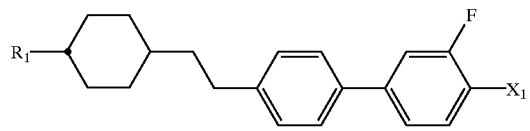
(3-27)
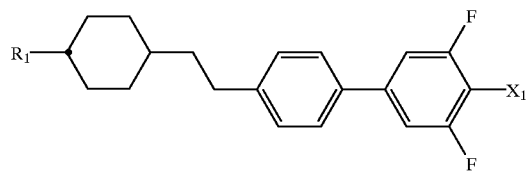
(3-28)
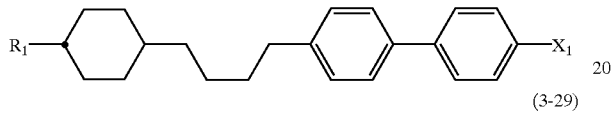
(3-29)
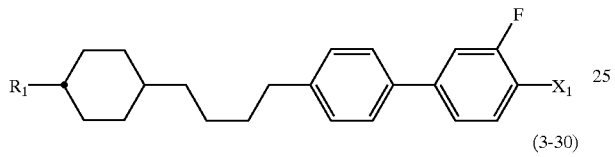
(3-30)
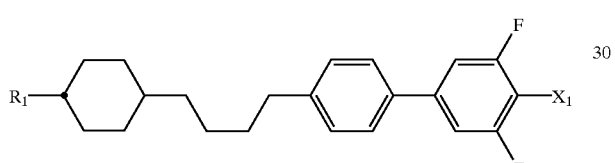
(3-31)
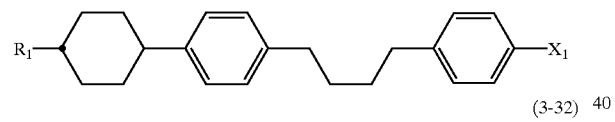
(3-32)
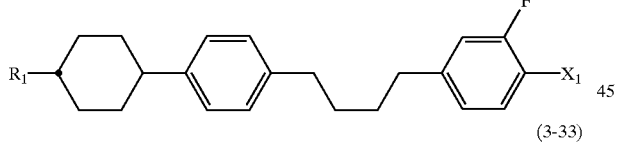
(3-33)
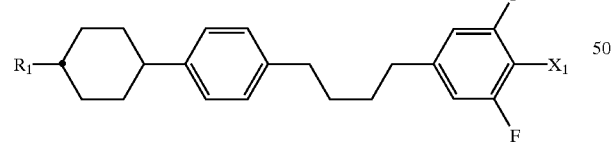
(3-34)
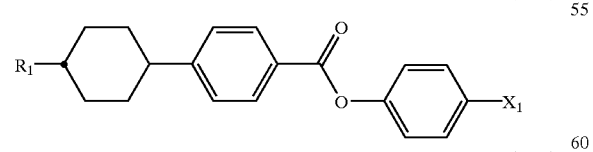
(3-35)
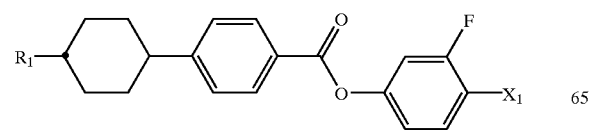
(3-36)
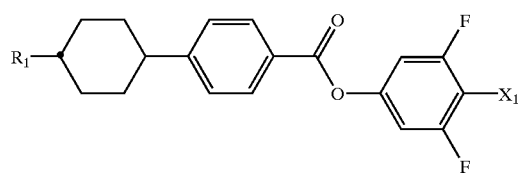
(3-37)
(3-38)
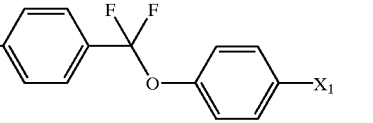
(3-39)
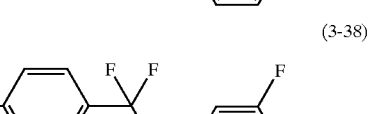
(3-40)
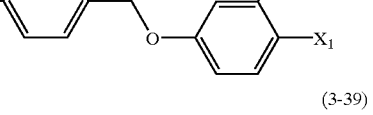
(3-41)
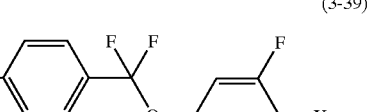
(3-42)
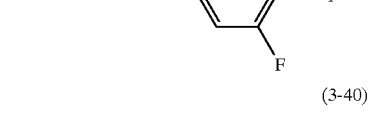
(3-43)
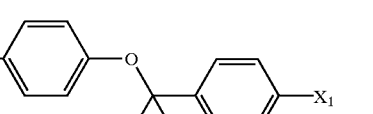
(3-44)

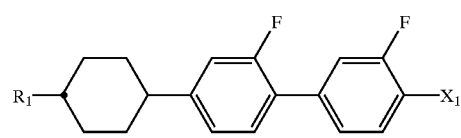 (3-45)
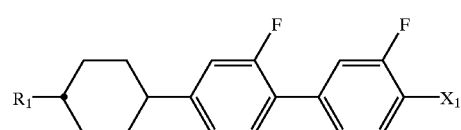 (3-46)
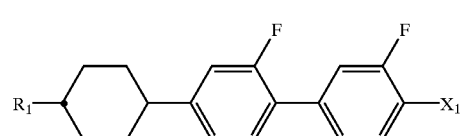 (3-47)
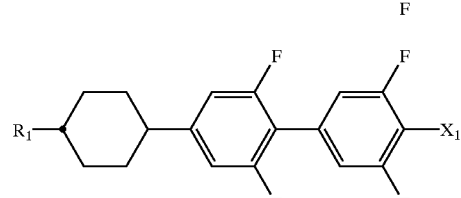 (3-48)
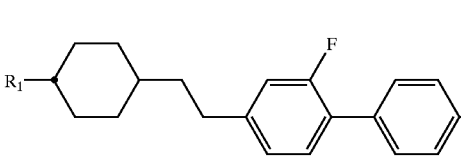 (3-49)
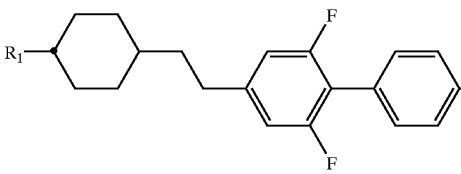 (3-50)
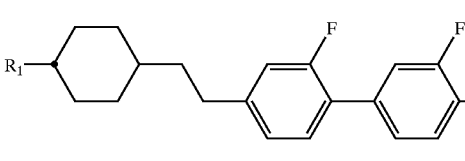 (3-51)
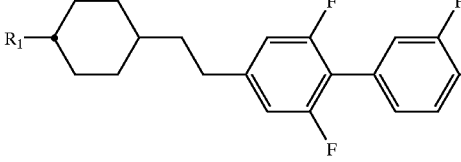 (3-52)
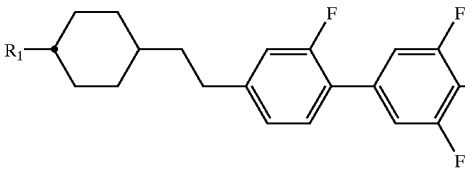 (3-53)
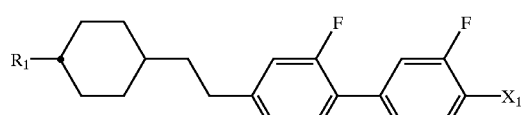 (3-54)
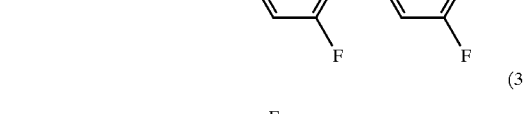 (3-55)
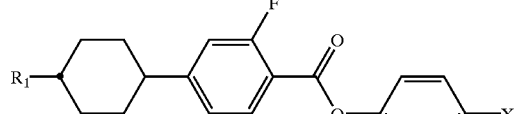 (3-56)
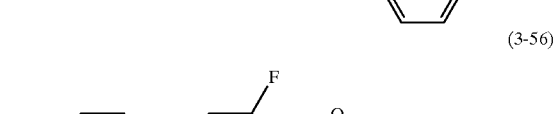 (3-57)
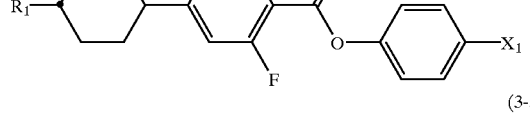 (3-58)
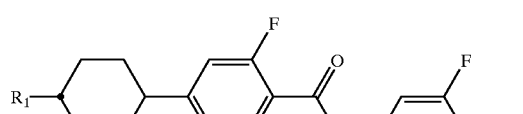 (3-59)
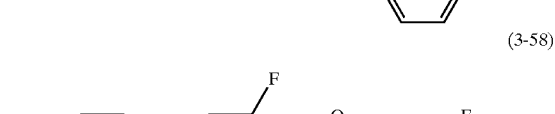 (3-60)
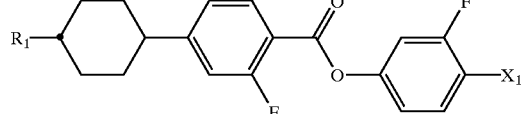 
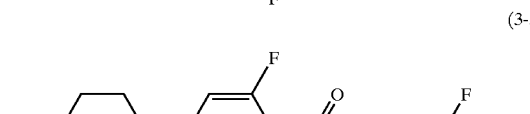 (3-61)
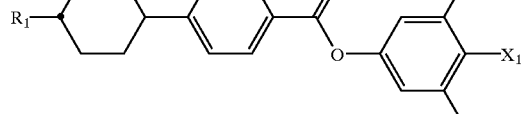
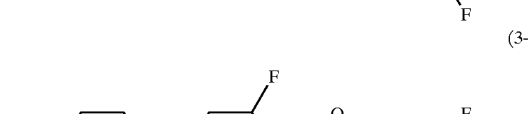
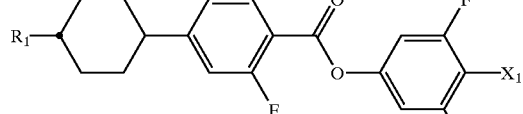
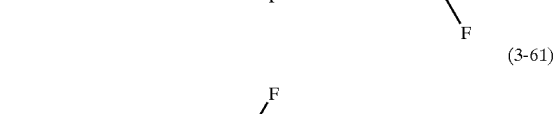
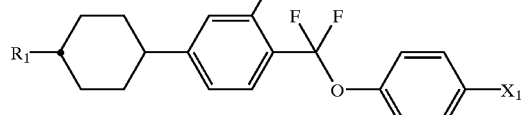

(3-62) 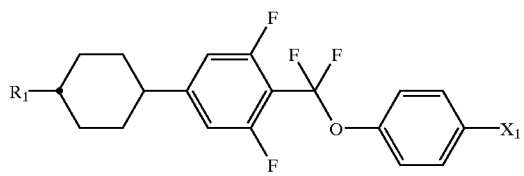
(3-63) 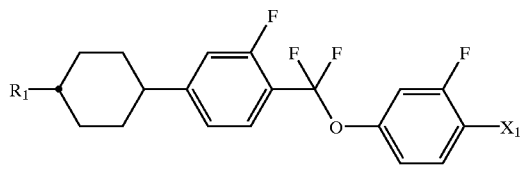
(3-64) 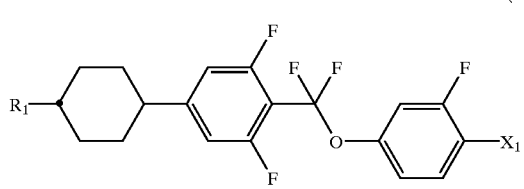
(3-65) 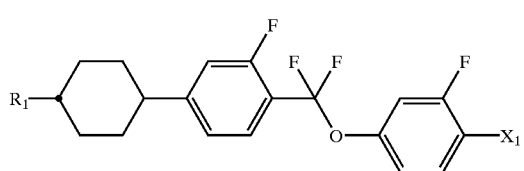
(3-66) 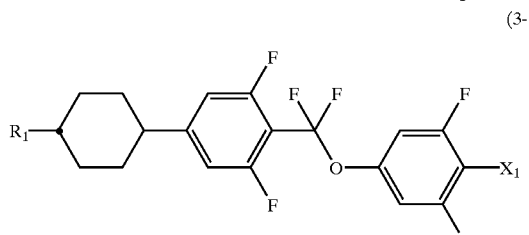
(3-67) 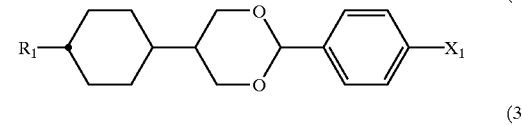
(3-68) 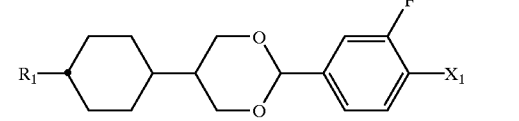
(3-69) 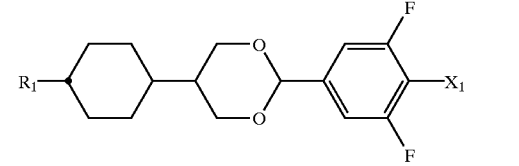
(4-1) 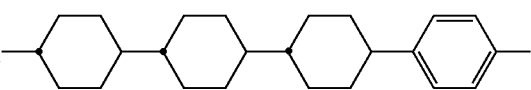
(4-2) 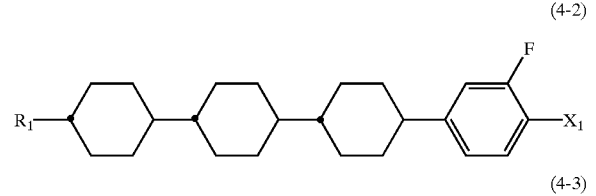
(4-3) 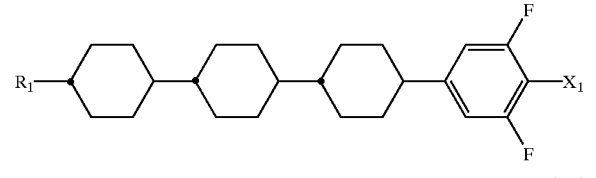
(4-4) 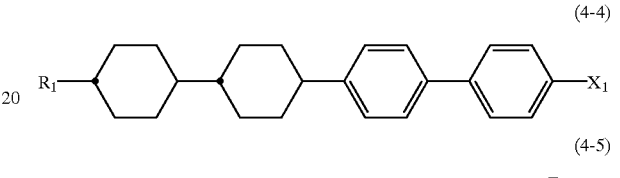
(4-5) 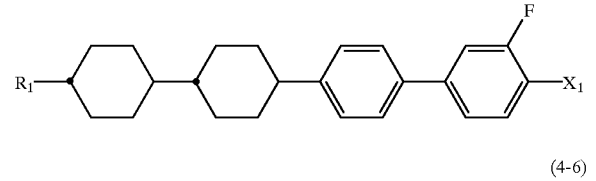
(4-6) 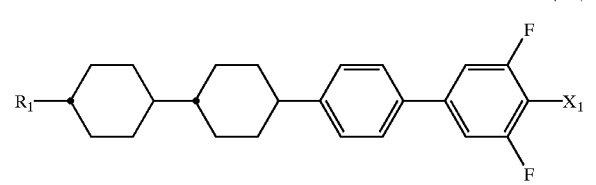
(4-7) 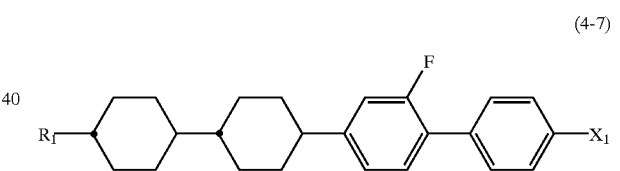
(4-8) 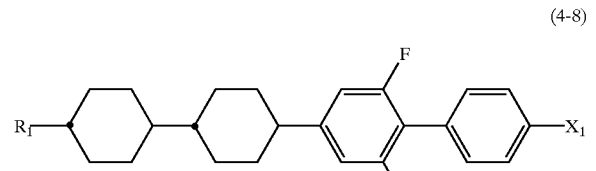
(4-9) 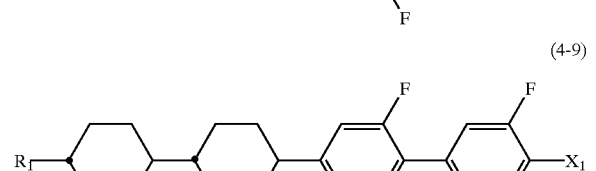
(4-10) 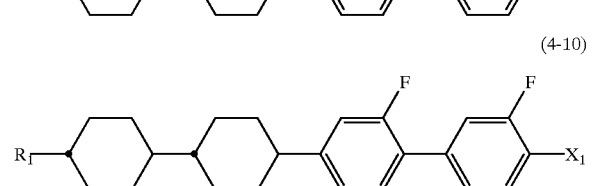

(4-11)
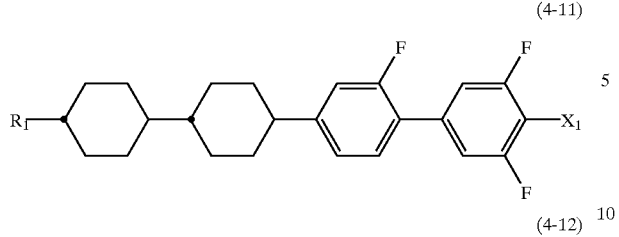

(4-12)
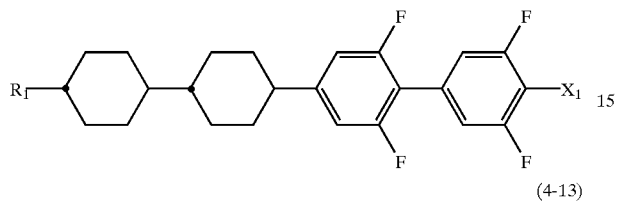

(4-13)
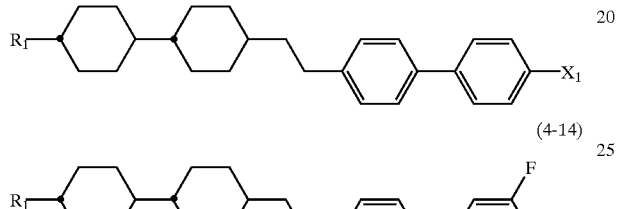

(4-14)
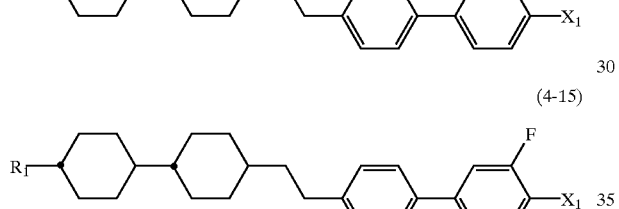

(4-15)
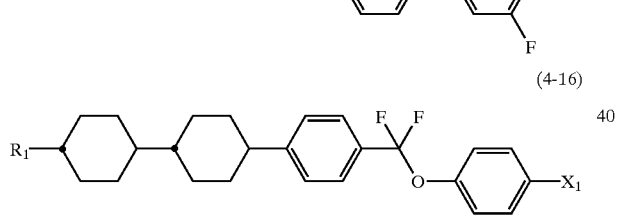

(4-16)
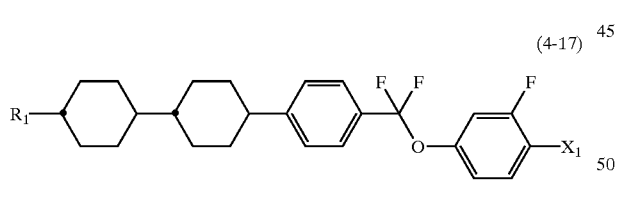

(4-17)
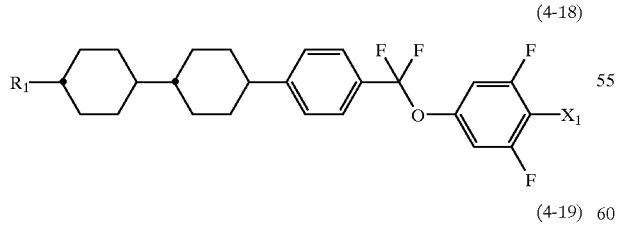

(4-18)
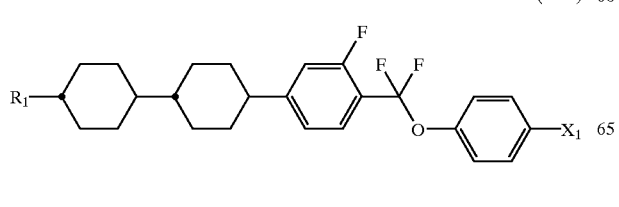

(4-19)
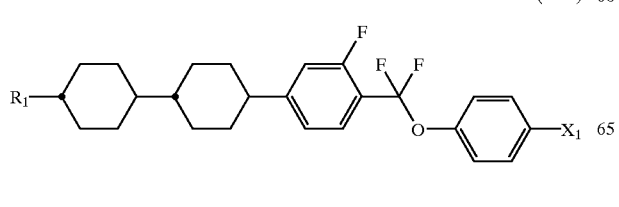

(4-20)
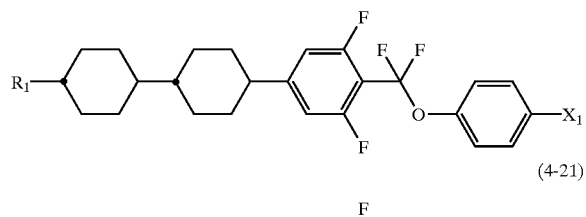

(4-21)
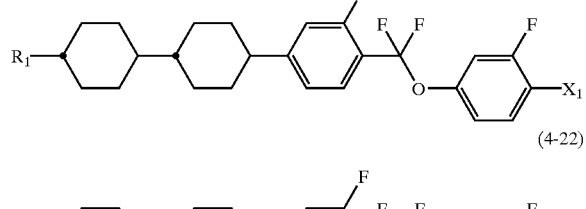

(4-22)
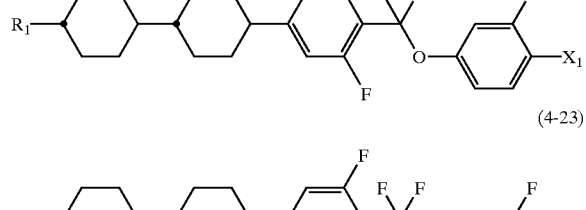

(4-23)
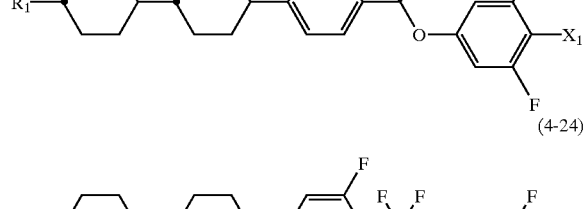

(4-24)
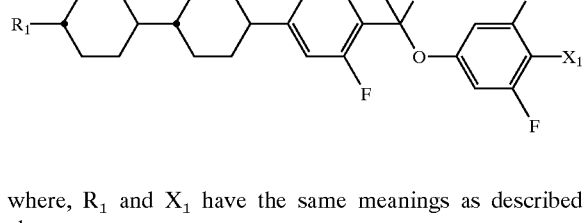

where, $R_1$ and $X_1$ have the same meanings as described above.

Compounds represented by general formulas (2) to (4) have positive dielectric anisotropys, excel in thermal and chemical stability, and are very useful for the preparation of liquid crystal compositions for TFT displays requiring high reliability; e.g., high voltage holding ratios and large resistivities.

In the preparation of liquid crystal compositions for TFT displays, the compounds represented by general formulas (2) to (4) can be used within the quantity range of 0.1 to 99.9% by weight, preferably 10 to 97% by weight, and more preferably 40 to 95% by weight. Compounds represented by general formulas (7) to (9) may further be contained for adjusting viscosity.

Although compounds represented by general formulas (2) to (4) can be used for preparing liquid crystal compositions for STN and TN displays, the total content of these compounds is preferably not more than 50% by weight.

Preferred examples of compounds represented by general formulas (5) and (6) used in the liquid crystal composition of the present invention are as follows:

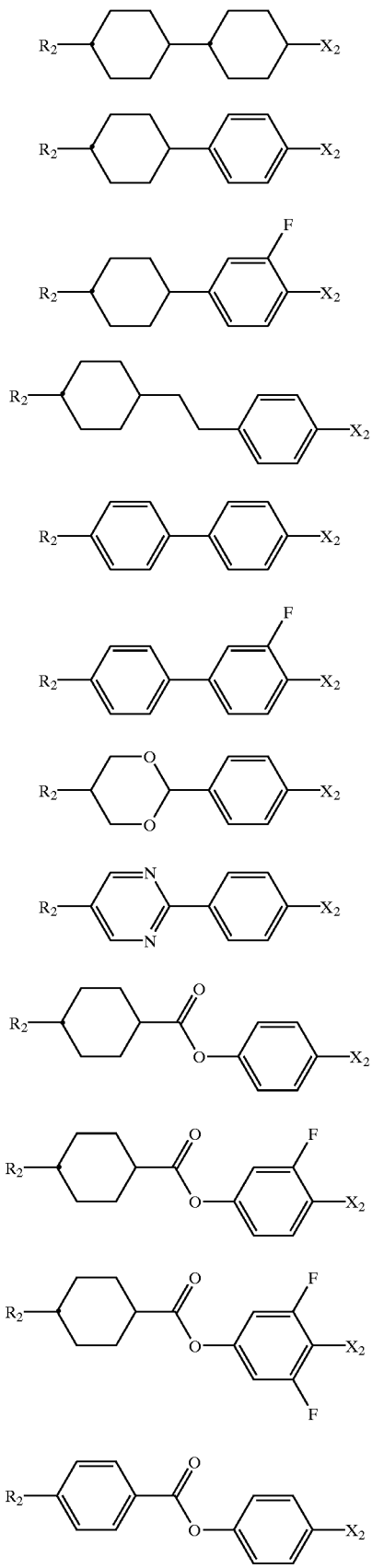
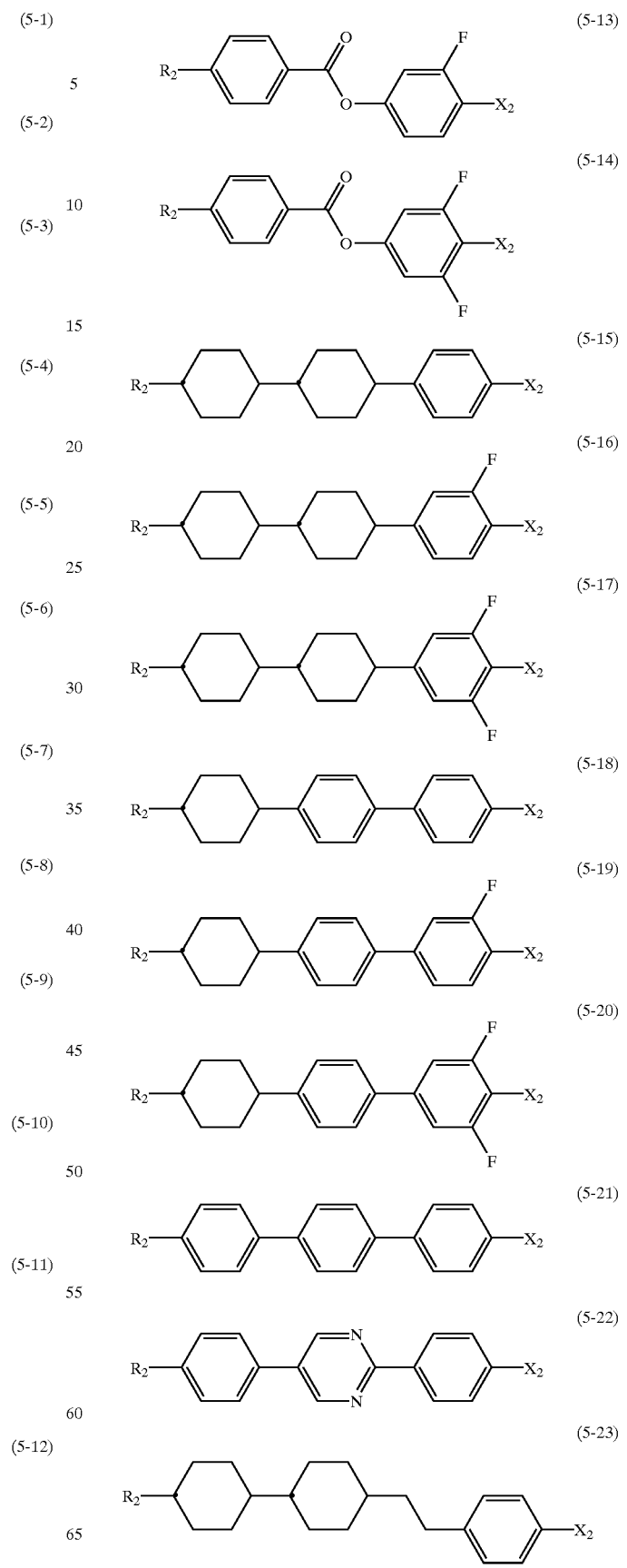

(5-24) 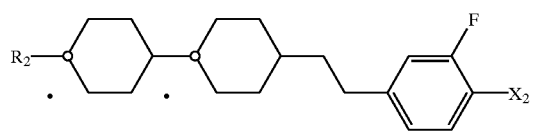
(5-25) 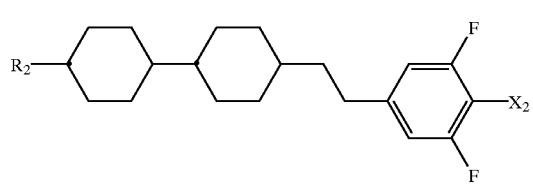
(5-26) 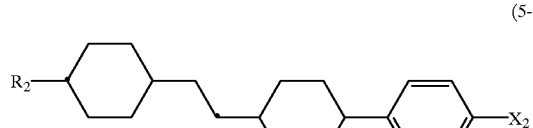
(5-27) 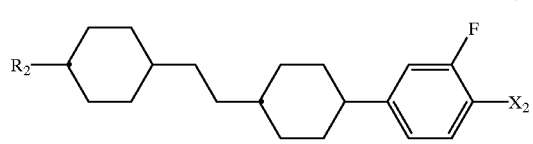
(5-28) 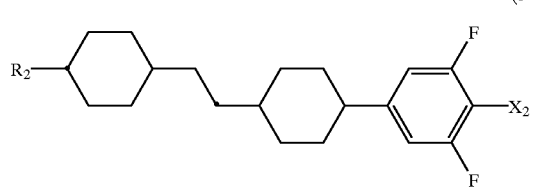
(5-29)
(5-30)
(5-31)
(5-32) 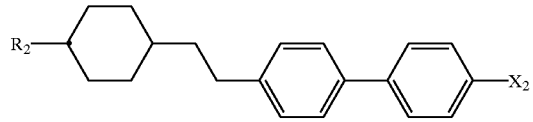
(5-33) 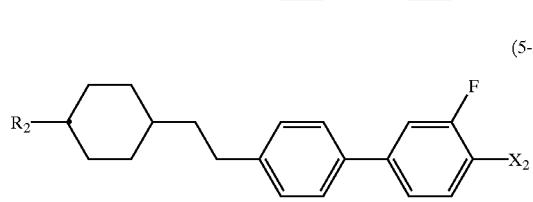
(5-34)
(5-35)
(5-36)
(5-37) 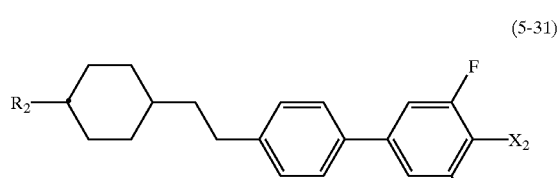
(5-38)
(5-39)
(5-40)
(6-1) 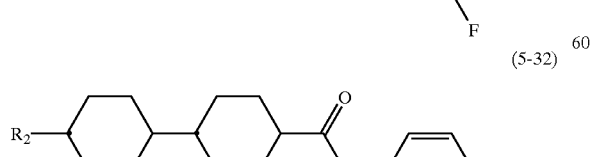
(6-2)

(6-3)

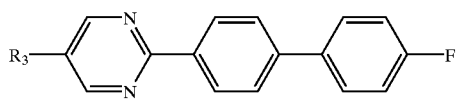

where, $R_2$, $R_3$, and $X_2$ have the same meanings as described above.

Compounds represented by general formulas (5) and (6) have large, positive dielectric anisotropys, and are used for lowering the threshold voltages of the liquid crystal composition. These compounds are also used for expanding the nematic range by adjusting optical anisotropy or elevating transparency points. Furthermore, these compounds are also used for the improvement of steepness of the liquid crystal compositions for STN or TN displays.

Compounds represented by general formulas (5) to (6) are particularly useful for the preparation of liquid crystal compositions for STN or TN displays.

When the quantity of compounds represented by general formulas (5) to (6) used in a liquid crystal composition increases, the threshold voltage of the liquid crystal composition decreases, but its viscosity increases. Therefore, so long as the viscosity of the liquid crystal composition satisfies the requirements, use of a greater quantity of the compounds is advantageous, because the displays can be driven at a lower voltage. In the preparation of liquid crystal compositions for STN or TN displays, the compounds represented by general formulas (5) and (6) can be used within the quantity range of 0.1 to 99.9% by weight, preferably 10 to 97% by weight, and more preferably 40 to 95% by weight.

Preferred examples of compounds represented by general formulas (7) to (9) used in the liquid crystal composition of the present invention are as follows:

(7-1)
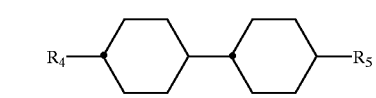

(7-2)
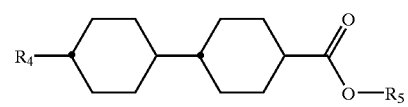

(7-3)
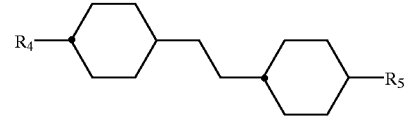

(7-4)
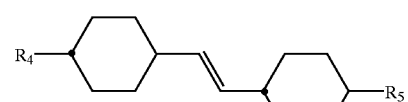

(7-5)
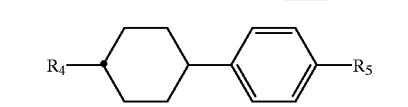

(7-6)
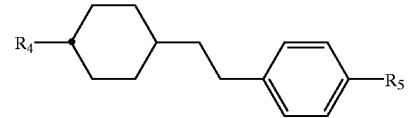

(7-7)
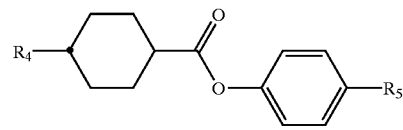

(7-8)
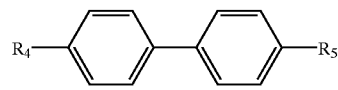

(7-9)
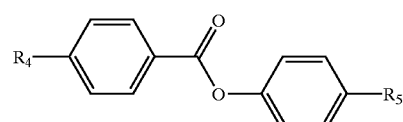

(7-10)
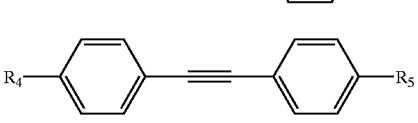

(7-11)
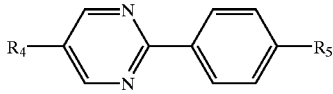

(8-1)
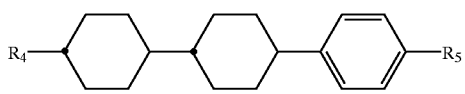

(8-2)
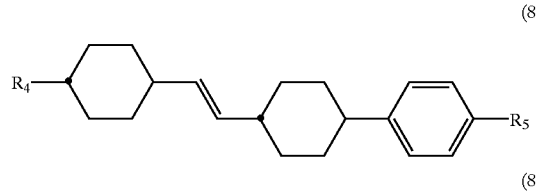

(8-3)
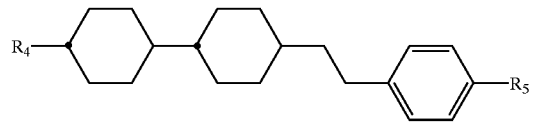

(8-4)
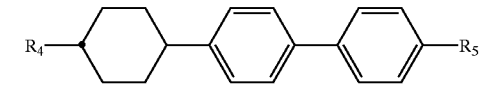

(8-5)
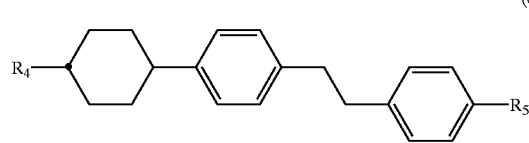

(8-6)
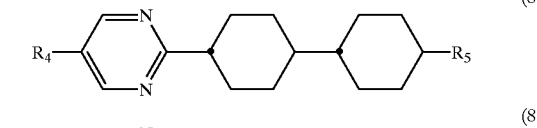

(8-7)
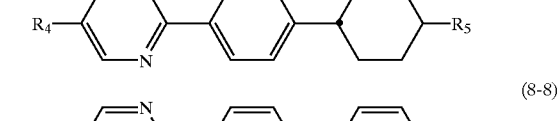

(8-8)

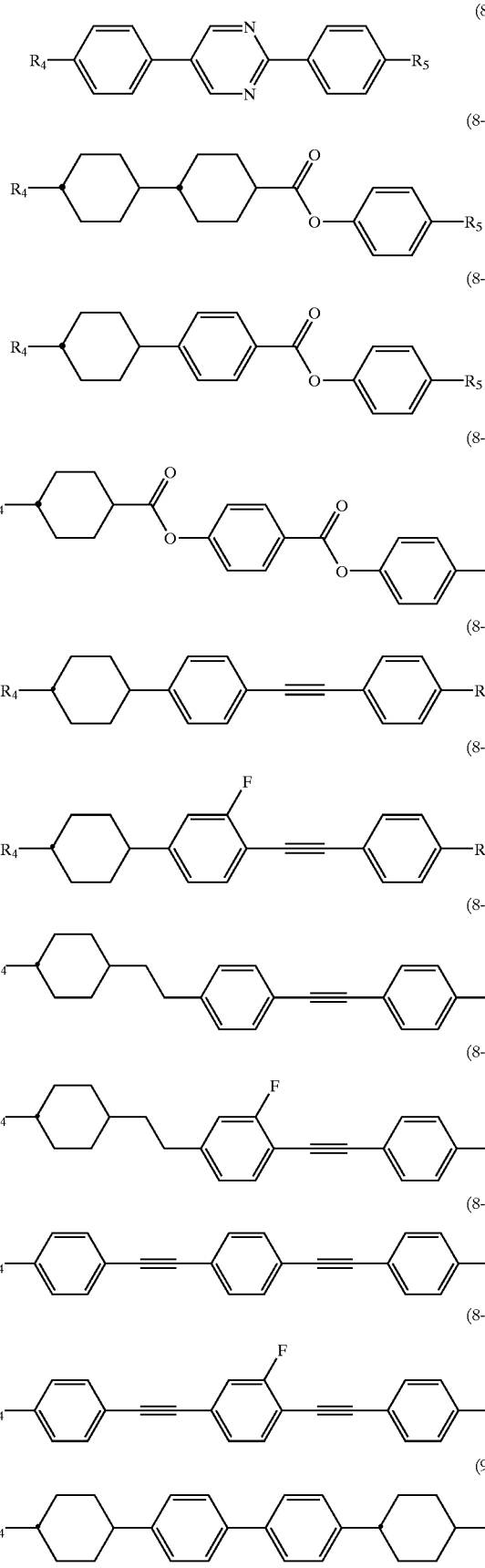
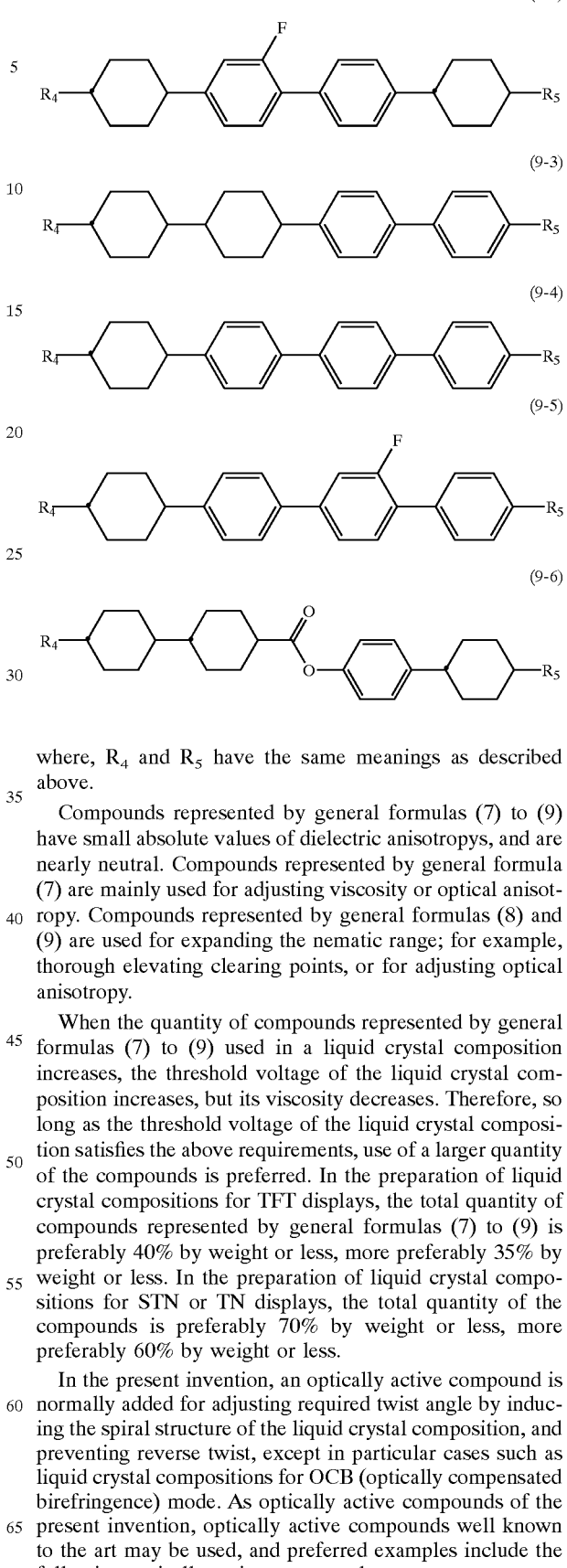

where, $R_4$ and $R_5$ have the same meanings as described above.

Compounds represented by general formulas (7) to (9) have small absolute values of dielectric anisotropys, and are nearly neutral. Compounds represented by general formula (7) are mainly used for adjusting viscosity or optical anisotropy. Compounds represented by general formulas (8) and (9) are used for expanding the nematic range; for example, thorough elevating clearing points, or for adjusting optical anisotropy.

When the quantity of compounds represented by general formulas (7) to (9) used in a liquid crystal composition increases, the threshold voltage of the liquid crystal composition increases, but its viscosity decreases. Therefore, so long as the threshold voltage of the liquid crystal composition satisfies the above requirements, use of a larger quantity of the compounds is preferred. In the preparation of liquid crystal compositions for TFT displays, the total quantity of compounds represented by general formulas (7) to (9) is preferably 40% by weight or less, more preferably 35% by weight or less. In the preparation of liquid crystal compositions for STN or TN displays, the total quantity of the compounds is preferably 70% by weight or less, more preferably 60% by weight or less.

In the present invention, an optically active compound is normally added for adjusting required twist angle by inducing the spiral structure of the liquid crystal composition, and preventing reverse twist, except in particular cases such as liquid crystal compositions for OCB (optically compensated birefringence) mode. As optically active compounds of the present invention, optically active compounds well known to the art may be used, and preferred examples include the following optically active compounds.

C15
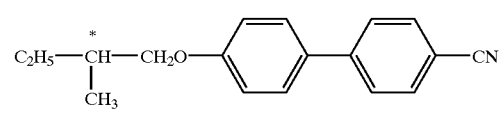

CB15
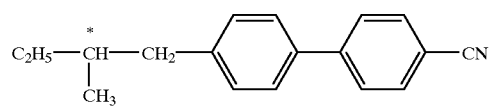

CM21
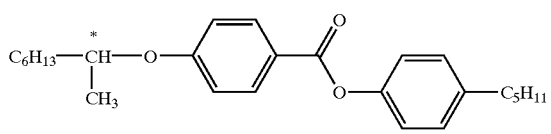

CM33
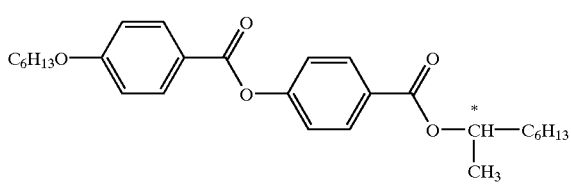

CM44
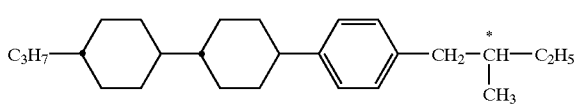

CM45
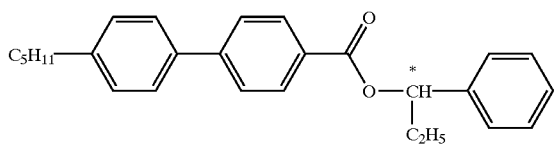

CM47
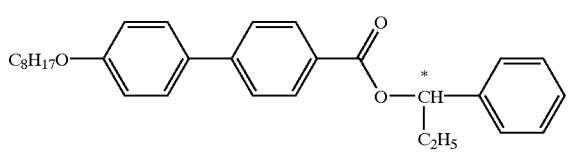

CN
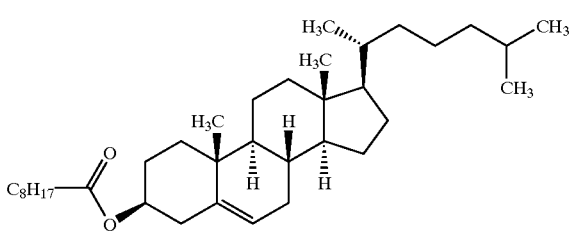

Normally, these optically active compounds are added to the liquid crystal composition of the present invention for adjusting the pitch of twist. The pitch of twist is preferably adjusted within a range of 40 to 200 $\mu$m for liquid crystal compositions for TFT and TN mode displays, and within a range of 6 to 20 $\mu$m for liquid crystal compositions for STN mode displays. For bistable TN mode displays, the pitch of twist is preferably adjusted within a range of 1.5 to 4 $\mu$m. Two or more optically active compounds may be added for adjusting the temperature dependence of the pitch.

The liquid crystal compositions of the present invention are prepared by commonly used techniques. Typically, various components are dissolved with each other at high temperature.

The liquid crystal compositions of the present invention can also be used as the liquid crystal compositions for guest-host (GH) mode displays by addition of dichromatic colorants such as merocyanine, styryl, azo, azomethyne, azoxy, quinophthalone, anthraquinone, and tetrazine dyes. The liquid crystal compositions of the present invention can also be used as the liquid crystal compositions for NCAPs produced by encapsulating nematic liquid crystals in micro capsules, or polymer dispersion-type liquid crystal display (PDLCD) elements represented by polymer network liquid crystal display (PNLCD) elements in which a three-dimensional matrix is formed in liquid crystals. In addition, such compositions can also be used as liquid crystal compositions for birefringence control (ECB) mode or dynamic scattering (DS) mode displays.

Examples of liquid crystal compositions containing the compounds of the present invention include the following. Compounds in the examples and in embodiments described below are represented by abbreviations according to the rules shown below. Compound numbers are the same as those shown in embodiments described below. In examples and embodiments, "percentage" means "percentage by weight" unless otherwise specified.

| Rc—Aa—Za— - - - - - - - —Zn—Ao—Rd | |
|---|---|
| Left end group: Rc | |
| $C_aH_{2a+1}$— | a— |
| $C_aH_{2a+1}O$— | aO— |
| $C_aH_{2a+1}OC_bH_{2b}$— | aOb— |
| $C_aH_{2a+1}OC_bH_{2b}O$— | aObO— |
| $C_{a-1}H_{2(a-1)+1}C(C_bH_{2b+1})HC_cH_{2c}$— | a(b)c— |
| $CFH_2C_{a-1}H_{2(a-1)}$— | Fa— |
| $CF_2HC_{a-1}H_{2(a-1)}$— | FFa— |
| $CF_3C_{a-1}H_{2(a-1)}$— | FFF1— |
| $CFH_2C_{a-1}H_{2(a-1)}O$— | FaO— |
| $CFH_2C_{a-1}H_{2(a-1)}OC_bH_{2b}$— | FaOb— |
| $C_aH_{2a+1}CFHC_bH_{2b}$— | a(F)b— |
| $C_aH_{2a+1}CF_2C_bH_{2b}$— | a(FF)b— |
| $C_aH_{2a+1}CH{=}CHC_bH_{2b}$— | aVb— |
| $C_aH_{2a+1}CH{=}CHC_bH_{2b}CH{=}CHC_cH_{2c}$— | aVbVc— |
| $C_aH_{2a+1}CH{=}CHC_bH_{2b}OC_cH_{2c}$— | aVbOc— |
| $C_aH_{2a+1}OC_bH_{2b}CH{=}CHC_cH_{2c}$— | aObVc— |
| $CFH_2C_{a-1}H_{2(a-1)}CH{=}CHC_bH_{2b}$— | FaVb— |
| $FFC{=}CHC_aH_{2a}$— | FFVa— |
| $F(CN)C{=}CHC_1H_{2a}$— | FCVa— |
| Bonding group: Za—Zn | |
| —$(CH_2)_a$— | a |
| —$CH_2O$— | $CH_2O$ |
| —$OCH_2$— | $OCH_2$ |
| —$C_3H_6O$— | $C_3H_6O$ |
| —$OC_3H_6$— | $OC_3H_6$ |
| —COO— | E |
| —C≡C— | T |
| —CH=CH— | V |
| —$CF_2O$— | $CF_2O$ |
| —$OCF_2$— | $OCF_2$ |

| Left end group: Rc | |
|---|---|
|  | B |
| 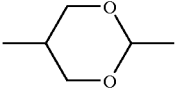 | B(2F) |
| 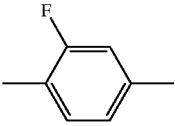 | B(F) |
| 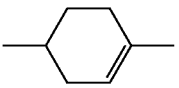 | B(Cl) |
| 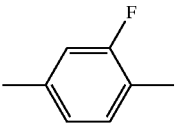 | B(2,3F) |
| 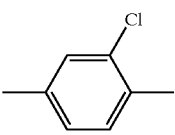 | B(2,3Cl) |
| 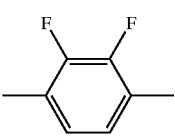 | B(F,F) |
| 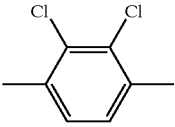 | B(F,Cl) |
| 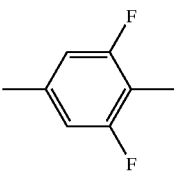 | H |
| 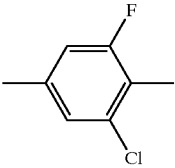 | Py |

-continued

| | |
|---|---|
| 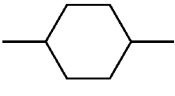 | D |
| 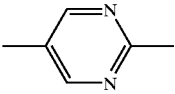 | Ch |

| Right end group: Rd | |
|---|---|
| —F | —F |
| —Cl | —CL |
| —CN | —C |
| —CF$_3$ | —CF3 |
| —OCF$_3$ | —OCF3 |
| —OCF$_2$H | —OCF2H |
| —OCF$_2$CF$_2$H | —OCF2CF2H |
| —OCF$_2$CFHCF$_3$ | —OCF2CFHCF3 |
| —C$_w$H$_{2w+1}$ | —w |
| —OC$_w$H$_{2w+1}$ | —Ow |
| —C$_w$H$_{2w}$CH=CH$_2$ | —wV |
| —C$_w$H$_{2w}$CH=CHC$_x$H$_{2x+1}$ | —wVx |
| —COOCH$_3$ | —EMe |
| —C$_w$H$_{2w}$CH=CHC$_x$H$_{2x}$F | —wVxF |
| —CH=CF$_2$ | —VFF |
| —C$_w$H$_{2w}$CH=CF$_2$ | —wVFF |
| —C≡C—CN | —TC |

COMPOSITION EXAMPLE 1

| | | |
|---|---|---|
| 3-B2B(F)B(F,F)—F | (Compound No. 13) | 10.0% |
| 1V2-BEB(F,F)—C | | 5.0% |
| 3-HB—C | | 25.0% |
| 1-BTB-3 | | 5.0% |
| 3-HH-4 | | 11.0% |
| 3-HHB-1 | | 11.0% |
| 3-HHB-3 | | 9.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 6.0% |

COMPOSITION EXAMPLE 2

| | | |
|---|---|---|
| 3-B(F)2B(F)B(F,F)—F | (Compound No. 1) | 6.0% |
| 3-B(F)2B(F,F)B(F)—F | (Compound No. 68) | 6.0% |
| V2-HB—C | | 12.0% |
| 1V2-HB—C | | 12.0% |
| 3-HB—C | | 12.0% |
| 3-HB(F)—C | | 5.0% |
| 2-BTB-1 | | 2.0% |
| 3-HH-4 | | 8.0% |
| 3-HH—VFF | | 6.0% |
| 2-HHB—C | | 3.0% |
| 3-HHB—C | | 6.0% |
| 3-HB(F)TB-2 | | 8.0% |
| 3-H2BTB-2 | | 5.0% |
| 3-H2BTB-3 | | 5.0% |
| 3-H2BTB-4 | | 4.0% |

COMPOSITION EXAMPLE 3

| | | |
|---|---|---|
| 3-B(F)2B(F,F)B(F)—CL | (Compound No. 71) | 5.0% |
| 3-BB(F,F)2B(F)—CL | (Compound No. 115) | 2.0% |
| 3O1-BEB(F)—C | | 13.0% |
| 4O1-BEB(F)—C | | 13.0% |
| 5O1-BEB(F)—C | | 13.0% |
| 2-HHB(F)—C | | 15.0% |
| 3-HHB(F)—C | | 15.0% |
| 3-HB(F)TB-2 | | 4.0% |
| 3-HB(F)TB-3 | | 4.0% |
| 3-HB(F)TB-4 | | 4.0% |
| 3-HHB-1 | | 8.0% |
| 3-HHB—O1 | | 4.0% |

COMPOSITION EXAMPLE 4

| | | |
|---|---|---|
| 3-B(F)2B(F)B(F,F)—F | (Compound No. 1) | 5.0% |
| 5-PyB—F | | 4.0% |
| 3-PyB(F)—F | | 4.0% |
| 2-BB—C | | 5.0% |
| 4-BB—C | | 4.0% |
| 5-BB—C | | 5.0% |
| 2-PyB-2 | | 2.0% |
| 3-PyB-2 | | 2.0% |
| 4-PyB-2 | | 2.0% |
| 6-PyB—O5 | | 3.0% |
| 6-PyB—O6 | | 3.0% |
| 6-PyB—O7 | | 3.0% |
| 6-PyB—O8 | | 3.0% |
| 3-PyBB—F | | 6.0% |
| 4-PyBB—F | | 6.0% |
| 5-PyBB—F | | 6.0% |
| 3-HHB-1 | | 6.0% |
| 3-HHB-3 | | 8.0% |
| 2-H2BTB-2 | | 4.0% |
| 2-H2BTB-3 | | 4.0% |
| 2-H2BTB-4 | | 5.0% |
| 3-H2BTB-2 | | 5.0% |
| 3-H2BTB-3 | | 5.0% |

COMPOSITION EXAMPLE 5

| | | |
|---|---|---|
| 3-B(F)2B(F,F)B(F)—F | (Compound No. 68) | 10.0% |
| 3-DB—C | | 10.0% |
| 2-BEB—C | | 12.0% |
| 3-BEB—C | | 4.0% |
| 3-PyB(F)—F | | 6.0% |
| 3-HEB—O4 | | 8.0% |
| 4-HEB—O2 | | 6.0% |
| 5-HEB—O1 | | 6.0% |
| 3-HEB—O2 | | 5.0% |
| 5-HEB—O2 | | 4.0% |
| 5-HEB-5 | | 5.0% |
| 4-HEB-5 | | 5.0% |
| 1O—BEB-2 | | 4.0% |
| 3-HHB-1 | | 6.0% |
| 3-HHEBB—C | | 3.0% |
| 3-HBEBB—C | | 3.0% |
| 5-HBEBB—C | | 3.0% |

COMPOSITION EXAMPLE 6

| | | |
|---|---|---|
| 3-BB(F,F)2B(F)—CL | (Compound No. 115) | 3.0% |
| 3-B2B(F)B(F,F)—F | (Compound No. 13) | 7.0% |
| 3-HB—C | | 18.0% |
| 1O1-HB—C | | 10.0% |
| 3-HB(F)—C | | 10.0% |
| 2-PyB-2 | | 2.0% |
| 3-PyB-2 | | 2.0% |
| 4-PyB-2 | | 2.0% |
| 2-BTB—O1 | | 7.0% |
| 3-HHB-1 | | 7.0% |
| 3-HHB—F | | 4.0% |
| 3-HHB—O1 | | 4.0% |
| 3-HB—O2 | | 8.0% |
| 3-H2BTB-2 | | 3.0% |
| 3-H2BTB-3 | | 3.0% |
| 2-PyBH-3 | | 4.0% |
| 3-PyBH-3 | | 3.0% |
| 3-PyBB-2 | | 3.0% |

COMPOSITION EXAMPLE 7

| | | |
|---|---|---|
| 3-B(F)2BB(F)—CF$_2$H | (Compound No. 11) | 3.0% |
| 2O1-BEB(F)—C | | 5.0% |
| 3O1-BEB(F)—C | | 9.0% |
| 5O1-BEB(F)—C | | 4.0% |
| 1V2-BEB(F,F)—C | | 10.0% |
| 3-HH-EMe | | 10.0% |
| 3-HB—O2 | | 18.0% |
| 7-HEB—F | | 2.0% |
| 3-HHEB—F | | 2.0% |
| 5-HHEB—F | | 2.0% |
| 3-HBEB—F | | 4.0% |
| 2O1-HBEB(F)—C | | 2.0% |
| 3-HB(F)EB(F)—C | | 2.0% |
| 3-HBEB(F,F)—C | | 2.0% |
| 3-HHB—F | | 4.0% |
| 3-HHB—O1 | | 4.0% |
| 3-HHB—3 | | 13.0% |
| 3-HEBEB—F | | 2.0% |
| 3-HEBEB—1 | | 2.0% |

COMPOSITION EXAMPLE 8

| | | |
|---|---|---|
| 3-B2B(F)B(F,F)—F | (Compound No. 13) | 2.0% |
| 3-B(F)2BB(F)—CF$_2$H | (Compound No. 11) | 2.0% |
| 5-BEB(F)—C | | 5.0% |
| V—HB—C | | 11.0% |
| 5-PyB—C | | 6.0% |
| 4-BB-3 | | 7.0% |
| 3-HH-2V | | 10.0% |
| 5-HH—V | | 11.0% |
| V—HHB-1 | | 7.0% |
| V2-HHB-1 | | 15.0% |
| 3-HHB-1 | | 9.0% |
| 1V2-HBB-2 | | 10.0% |
| 3-HHEBH-3 | | 5.0% |

COMPOSITION EXAMPLE 9

| | | |
|---|---|---|
| 3-B(F)B(F)2B(F,F)—OCF$_2$H | (Compound No. 159) | 2.0% |
| 3-B(F,F)B(F)2B(F,F)—CFH$_2$ | (Compound No. 193) | 2.0% |
| 2O1-BEB(F)—C | | 5.0% |
| 3O1-BEB(F)—C | | 12.0% |
| 5O1-BEB(F)—C | | 4.0% |
| 1V2-BEB(F,F)—C | | 16.0% |
| 3-HB—O2 | | 10.0% |
| 3-HH-4 | | 3.0% |

-continued

| | |
|---|---|
| 3-HHB—F | 3.0% |
| 3-HHB-1 | 8.0% |
| 3-HHB—O1 | 4.0% |
| 3-HBEB—F | 4.0% |
| 3-HHEB—F | 4.0% |
| 5-HHEB—F | 7.0% |
| 3-H2BTB-2 | 7.0% |
| 3-H2BTB-3 | 4.0% |
| 3-HB(F)TB-2 | 5.0% |

COMPOSITION EXAMPLE 10

| | | |
|---|---|---|
| 3-B2B(F)B(F,F)—F | (Compound No. 13) | 2.0% |
| 3-B(F)2B(F)B(F,F)—F | (Compound No. 1) | 2.0% |
| 3-B(F)2B(F,F)B(F)—F | (Compound No. 68) | 2.0% |
| 3-BB(F,F)2B(F)—CL | (Compound No. 115) | 2.0% |
| 2-BEB—C | | 12.0% |
| 3-BEB—C | | 4.0% |
| 4-BEB—C | | 6.0% |
| 3-HB—C | | 20.0% |
| 3-HEB—O4 | | 12.0% |
| 4-HEB—O2 | | 8.0% |
| 5-HEB—O1 | | 8.0% |
| 3-HEB—O2 | | 6.0% |
| 5-HEB—O2 | | 5.0% |
| 3-HHB-1 | | 7.0% |
| 3-HHB—O1 | | 4.0% |

COMPOSITION EXAMPLE 11

| | | |
|---|---|---|
| 3-B2B(F)B(F,F)—F | (Compound No. 13) | 2.0% |
| 3-BB(F,F)2B(F)—CL | (Compound No. 115) | 2.0% |
| 3-B(F)B(F)2B(F,F)—OCF₂H | (Compound No. 159) | 2.0% |
| 2-BEB—C | | 10.0% |
| 5-BB—C | | 12.0% |
| 7-BB—C | | 7.0% |
| 1-BTB-3 | | 7.0% |
| 2-BTB-1 | | 4.0% |
| 1O—BEB-2 | | 10.0% |
| 1O—BEB-5 | | 12.0% |
| 2-HHB-1 | | 4.0% |
| 2-HHB—F | | 4.0% |
| 3-HHB-1 | | 7.0% |
| 3-HHB—O1 | | 4.0% |
| 3-HHB-3 | | 13.0% |

COMPOSITION EXAMPLE 12

| | | |
|---|---|---|
| 3-B2B(F)B(F,F)—F | (Compound No. 13) | 3.0% |
| 3-B(F)2B(F)B(F,F)—F | (Compound No. 1) | 2.0% |
| 3-B(F)2B(F,F)B(F)—F | (Compound No. 68) | 2.0% |
| 2-HHB(F)—F | | 17.0% |
| 3-HHB(F)—F | | 17.0% |
| 5-HHB(F)—F | | 16.0% |
| 2-H2HB(F)—F | | 10.0% |
| 3-H2HB(F)—F | | 5.0% |
| 5-H2HB(F)—F | | 10.0% |
| 2-HBB(F)—F | | 6.0% |
| 3-HBB(F)—F | | 6.0% |
| 5-HBB(F)—F | | 6.0% |

COMPOSITION EXAMPLE 13

| | | |
|---|---|---|
| 3-B2B(F)B(F,F)—F | (Compound No. 13) | 5.0% |
| 3-B(F)2B(F,F)B(F)—CL | (Compound No. 71) | 2.0% |
| 7-HB(F)—F | | 5.0% |
| 5-H2B(F)—F | | 5.0% |
| 3-HB—O2 | | 10.0% |
| 3-HH-4 | | 5.0% |
| 2-HHB(F)—F | | 8.0% |
| 3-HHB(F)—F | | 10.0% |
| 5-HHB(F)—F | | 5.0% |
| 3-H2HB(F)—F | | 5.0% |
| 2-HBB(F)—F | | 3.0% |
| 3-HBB(F)—F | | 3.0% |
| 5-HBB(F)—F | | 6.0% |
| 2-H2BB(F)—F | | 5.0% |
| 3-H2BB(F)—F | | 6.0% |
| 3-HHB-1 | | 8.0% |
| 3-HHB—O1 | | 5.0% |
| 3-HHB-3 | | 4.0% |

COMPOSITION EXAMPLE 14

| | | |
|---|---|---|
| 3-B2B(F)B(F,F)—F | (Compound No. 13) | 5.0% |
| 7-HB(F,F)—F | | 3.0% |
| 3-HB—O2 | | 7.0% |
| 2-HHB(F)—F | | 10.0% |
| 3-HHB(F)—F | | 10.0% |
| 5-HHB(F)—F | | 10.0% |
| 2-HBB(F)—F | | 9.0% |
| 3-HBB(F)—F | | 9.0% |
| 5-HBB(F)—F | | 16.0% |
| 2-HBB—F | | 4.0% |
| 3-HBB—F | | 4.0% |
| 5-HBB—F | | 3.0% |
| 3-HBB(F,F)—F | | 5.0% |
| 5-HBB(F,F)—F | | 5.0% |
| 5-HHB(F)—F | | 10.0% |
| 2-HBB(F)—F | | 9.0% |
| 3-HBB(F)—F | | 9.0% |
| 5-HBB(F)—F | | 16.0% |
| 2-HBB—F | | 4.0% |
| 3-HBB—F | | 4.0% |
| 5-HBB—F | | 3.0% |
| 3-HBB(F,F)—F | | 5.0% |
| 5-HBB(F,F)—F | | 5.0% |

COMPOSITION EXAMPLE 15

| | | |
|---|---|---|
| 3-B(F)2B(F)B(F,F)—F | (Compound No. 1) | 7.0% |
| 7-HB(F,F)—F | | 4.0% |
| 3-H2HB(F,F)—F | | 5.0% |
| 4-H2HB(F,F)—F | | 10.0% |
| 5-H2HB(F,F)—F | | 10.0% |
| 3-HHB(F,F)—F | | 10.0% |
| 4-HHB(F,F)—F | | 5.0% |
| 3-HH2B(F,F)—F | | 15.0% |
| 5-HH2B(F,F)—F | | 10.0% |
| 3-HBB(F,F)—F | | 12.0% |
| 5-HBB(F,F)—F | | 12.0% |

COMPOSITION EXAMPLE 16

| | | |
|---|---|---|
| 3-B(F)2B(F,F)B(F)—F | (Compound No. 68) | 5.0% |
| 7-HB(F,F)—F | | 5.0% |

-continued

| | |
|---|---|
| 3-H2HB(F,F)—F | 12.0% |
| 4-H2HB(F,F)—F | 10.0% |
| 3-HHB(F,F)—F | 10.0% |
| 4-HHB(F,F)—F | 5.0% |
| 3-HBB(F,F)—F | 5.0% |
| 3-HHEB(F,F)—F | 10.0% |
| 4-HHEB(F,F)—F | 3.0% |
| 5-HHEB(F,F)—F | 3.0% |
| 2-HBEB(F,F)—F | 3.0% |
| 3-HBEB(F,F)—F | 5.0% |
| 5-HBEB(F,F)—F | 3.0% |
| 3-HDB(F,F)—F | 15.0% |
| 3-HHBB(F,F)—F | 6.0% |

COMPOSITION EXAMPLE 17

| | | |
|---|---|---|
| 3-B(F)2B(F,F)B(F)—CL | (Compound No. 71) | 2.0% |
| 3-BB(F,F)2B(F)—CL | (Compound No. 115) | 2.0% |
| 3-HB—CL | | 10.0% |
| 5-HB—CL | | 4.0% |
| 7-HB—CL | | 4.0% |
| 1O1-HH-5 | | 5.0% |
| 2-HBB(F)—F | | 8.0% |
| 3-HBB(F)—F | | 8.0% |
| 5-HBB(F)—F | | 10.0% |
| 4-HHB—CL | | 8.0% |
| 5-HHB—CL | | 8.0% |
| 3-H2HB(F)—CL | | 4.0% |
| 3-HBB(F,F)—F | | 10.0% |
| 5-H2BB(F,F)—F | | 9.0% |
| 3-HB(F)VB-2 | | 4.0% |
| 3-HB(F)VB-3 | | 4.0% |

COMPOSITION EXAMPLE 18

| | | |
|---|---|---|
| 3-B2B(F)B(F,F)—F | (Compound No. 13) | 2.0% |
| 3-B(F)2B(F)B(F,F)—F | (Compound No. 1) | 2.0% |
| 3-B(F)2B(F,F)-B(F)—F | (Compound No. 68) | 2.0% |
| 3-B(F)2B(F,F)-B(F)—CL | (Compound No. 71) | 2.0% |
| 3-BB(F,F)2B(F)—CL | (Compound No. 115) | 2.0% |
| 3-HHB(F,F)—F | | 9.0% |
| 3-H2HB(F,F)—F | | 8.0% |
| 4-H2HB(F,F)—F | | 8.0% |
| 5-H2HB(F,F)—F | | 8.0% |
| 3-HHB(F,F)—F | | 21.0% |
| 5-HHB(F,F)—F | | 10.0% |
| 3-H2BB(F,F)—F | | 10.0% |
| 5-HHBB(F,F)—F | | 3.0% |
| 3-HH2BB(F,F)—F | | 3.0% |
| 5-HHEBB—F | | 2.0% |
| 1O1-HBBH-4 | | 4.0% |
| 1O1-HBBH-5 | | 4.0% |

COMPOSITION EXAMPLE 19

| | | |
|---|---|---|
| 3-B2B(F)B(F,F)—F | (Compound No. 13) | 2.0% |
| 3-B(F)2BB(F)—CF$_2$H | (Compound No. 11) | 2.0% |
| 3-B(F)B(F)2B(F,F)—OCF$_2$H | (Compound No. 159) | 2.0% |
| 5-HB—F | | 12.0% |
| 6-HB—F | | 9.0% |
| 7-HB—F | | 7.0% |
| 2-HHB—OCF$_3$ | | 7.0% |
| 3-HHB—OCF$_3$ | | 11.0% |
| 4-HHB—OCF$_3$ | | 7.0% |
| 5-HHB—OCF$_3$ | | 5.0% |

-continued

| | |
|---|---|
| 3-HH2B—OCF$_3$ | 4.0% |
| 5-HH2B—OCF$_3$ | 4.0% |
| 3-HHB(F,F)—OCF$_3$ | 5.0% |
| 3-HBB(F)—F | 10.0% |
| 5-HBB(F)—F | 4.0% |
| 3-HH2B(F)—F | 3.0% |
| 3-HB(F)BH-3 | 3.0% |
| 5-HBBH-3 | 3.0% |

COMPOSITION EXAMPLE 20

| | | |
|---|---|---|
| 3-B(F)2B(F,F)B(F)—F | (Compound No. 68) | 5.0% |
| 3-B(F)2B(F,F)B(F)—CL | (Compound No. 71) | 5.0% |
| 5-H4HB(F,F)—F | | 7.0% |
| 5-H4HB—OCF$_3$ | | 10.0% |
| 3-H4HB(F,F)—CF$_3$ | | 8.0% |
| 5-H4HB(F,F)—CF$_3$ | | 5.0% |
| 3-HB—CL | | 6.0% |
| 5-HB—CL | | 4.0% |
| 2-H2BB(F)—F | | 5.0% |
| 3-H2BB(F)—F | | 10.0% |
| 5-HVHB(F,F)—F | | 5.0% |
| 3-HHB—OCF$_3$ | | 5.0% |
| 3-H2HB—OCF$_3$ | | 5.0% |
| V—HHB(F)—F | | 5.0% |
| 3-HChB(F)—F | | 5.0% |
| 5-HHEB—OCF$_3$ | | 2.0% |
| 3-HBEB(F,F)—F | | 5.0% |
| 5-HH—V2F | | 3.0% |

COMPOSITION EXAMPLE 21

| | | |
|---|---|---|
| 3-B2B(F)B(F,F)—F | (Compound No. 13) | 3.0% |
| 3-B(F)2B(F,F)B(F)—F | (Compound No. 68) | 3.0% |
| 3-B(F,F)B(F)2B(F,F)—CFH$_2$ | (Compound No. 193) | 3.0% |
| 2-HHB(F)—F | | 2.0% |
| 3-HHB(F)—F | | 2.0% |
| 5-HHB(F)—F | | 2.0% |
| 2-HBB(F)—F | | 6.0% |
| 3-HBB(F)—F | | 6.0% |
| 5-HBB(F)—F | | 10.0% |
| 2-H2BB(F)—F | | 9.0% |
| 3-H2BB(F)—F | | 9.0% |
| 3-HBB(F,F)—F | | 25.0% |
| 5-HBB(F,F)—F | | 10.0% |
| 1O1-HBBH-4 | | 5.0% |
| 1O1-HBBH-5 | | 5.0% |

BEST MODE FOR CARRYING OUT THE INVENTION

The present invention will be described in further detail by reference to embodiments. In each embodiment, C represents a crystal, SA represents a smectic phase A, SB represents a smectic phase B, SX represents a smectic phase not determined, N represents a nematic phase, and Iso represents an isotropic phase. The unit for all transition temperatures is ° C.

Embodiment 1

Synthesis of 4'-(2-(2-fluoro-4-propylphenyl)ethyl)-2'-fluoro-3,4,5-trifluorobiphenyl (compound (No. 1) represented by general formula (1), where R is $C_3H_7$, each of $Y_1$, $Y_3$, $Y_5$, $Y_6$, and X is F, $Z_1$ is —(CH$_2$)$_2$—, and $Z_2$ is a covalent bond)

(Step 1) Synthesis of (2-(2-fluoro-4-propylphenyl)ethyl)-3-fluoro-4-iodobenzene

Into a solution of 2.6 g (10.1 mmol) of (2-(2-fluoro-4-propylphenyl)ethyl)-3-fluorobenzene dissolved in 40 ml of tetrahydrofuran (THF), 11 ml (11.1 mmol) of sec-BuLi was added dropwise at a speed that maintains a temperature of −60° C. or below, and after completion of addition, the solution was stirred for 2 hours at the same temperature. Then, a solution of 2.9 g (11.6 mmol) of iodine dissolved in 20 ml of THF was added dropwise at a speed that maintains a temperature of −60° C. or below, and the solution was stirred for 1 hour at the same temperature.

After dropwise addition of 50 ml of 1N-HCl into the reaction solution, the solution was extracted with 50 ml of heptane. The organic layer obtained was washed three times with diluted $NaHCO_3$ solution and three times with water, and dried over anhydrous magnesium sulfate. The solvent was distilled off under a reduced pressure, and the residue was subjected to a silica gel column chromatograph to obtain 3.5 g of crude (2-(2-fluoro-4-propylphenyl)ethyl)-3-fluoro-4-iodobenzene (yield: 90.5%).

(Step 2) Synthesis of 4'-(2-(2-fluoro-4-propylphenyl)ethyl)-2'-fluoro-3,4,5-trifluorobiphenyl The mixture of 3.5 g (9.1 mmol) of (2-(2-fluoro-4-propylphenyl)ethyl)-3-fluoro-4-iodobenzene obtained in the previous step, 2.1 g (11.9 mmol) of dihydroxy(3,4,5-trifluorophenyl)borane, 2.5 g (18.3 mmol) of $K_2CO_3$, 0.3 g of 5% Pd—C, and 30 ml of a toluene/ethanol/water (1/1/1) mixed solvent was heated and refluxed for 12 hours. Then, after Pd—C was removed by filtration, the solution was extracted by 100 ml of toluene, and the obtained organic layer was washed three times with water and dried over anhydrous magnesium sulfate. The solvent was distilled off under reduced pressure, and the residue was subjected to a silica gel column chromatograph (eluent: heptane) to obtain 2.5 g of crude 4'-(2-(2-fluoro-4-propylphenyl)ethyl)-2'-fluoro-3,4,5-trifluorobiphenyl.

The product was recrystallized from ethanol to form 1.2 g of the desired compound (yield: 34.3%).

The transition temperature of this compound was: C 66.6–67.8 Iso

All spectrum data well supported its structure. Mass spectrometry: 390($M^+$)

$^1$H-NMR (CDCl$_3$, TMS internal standard) δ (ppm) 0.93 (t, 3H) 1.54–1.75 (m, 2H) 2.56 (t, 2H) 2.92 (s, 4H) 6.80–7.36 (m, 8H)

Examples of cases where the compounds of the present invention were used as the components of liquid crystal compositions will be shown below. In these examples, NI represents a nematic phase-isotropic transition temperature (° C.), Δε represents a dielectric anisotropy value, Δn represents an optical anisotropy value, η represents viscosity (mPa·s), Vth represents a threshold voltage (V), and τ represents a response time (ms) measured at driving voltage 2.5 V.

η was measured at 20° C., and Δε, Δn, Vth and τr were measured at 25° C.

Embodiment 2 (Use Example 1)

Liquid crystal composition (A) containing the following cyanophenyl cyclohexane liquid crystalline compounds:

| | |
|---|---|
| 4-(trans-4-propylcyclohexyl)benzonitrile | 24% |
| 4-(trans-4-pentylcyclohexyl)benzonitrile | 36% |
| 4-(trans-4-heptylcyclohexyl)benzonitrile | 25% |
| 4-(trans-4-pentylcyclohexyl)-4'-cyanobiphenyl | 15% | has the following properties:

NI: 71.7, Δε: 11.0, Δn: 0.137, η: 26.7, Vth: 1.78

The properties of liquid crystal composition (B) consisting of 85% composition (A) and 15% 4'-(2-(2-fluoro-4-propylphenyl)ethyl)-2'-fluoro-3,4,5-trifluorobiphenyl (compound No. 1) obtained in Embodiment 1 are as follows:

Δε: 12.4, Δn: 0.133, η: 30.2, Vth: 1.35

Although this liquid crystal composition (B) was stored in a freezer of a temperature of −20° C., neither appearance of a smectic phase nor deposition of crystals was observed even after 60 days.

Embodiment 3 (Use Example 2)

The following compounds can be synthesized according to the method of Embodiment 1. Properties shown here were measured in the same manner as in Embodiment 2.

Compound No. 2: 1-B(F)2BB(F,F)—F
Compound No. 3: 2-B(F)2BB(F)—F
Compound No. 4: 3-B(F)2BB(F,F)—CL
Compound No. 5: 5-B(F)2BB(F)—CL
Compound No. 6: 3O—B(F)2BB(F,F)—OCF$_3$
Compound No. 7: 3-B(F)2BB(F)—OCF$_3$
Compound No. 8: 4-B(F)2BB(F,F)—CF$_3$
Compound No. 9: 5-B(F)2BB(F)—CF$_3$
Compound No. 10: 1O3O—B(F)2BB(F,F)—CF$_2$H
Compound No. 11: 3-B(F)2BB(F,F)—CF$_2$H
Compound No. 12: 2-B(F)2BB(F)—CFH$_2$
Compound No. 13: 3-B2B(F)B(F,F)—F
Compound No. 14: 4-B2B(F)B(F,F)—CL
Compound No. 15: 5-B2B(F)B(F,F)—OCF$_3$
Compound No. 16: 6-B2B(F)B(F,F)—OCF$_2$H
Compound No. 17: 7-B2B(F)B(F,F)—CF$_3$
Compound No. 18: 1O—B2B(F)B(F,F)—CF$_2$H
Compound No. 19: 2O-B2B(F)B(F,F)—CF$_2$
Compound No. 20: 4-B(F,F)2BB(F,F)—F
Compound No. 21: 5-B(F,F)2BB(F)—F
Compound No. 22: 3O1-B(F,F)2BB(F,F)—CL
Compound No. 23: 3O1O—B(F,F)2BB(F)—CL
Compound No. 24: 3-B(F,F)2BB—CL
Compound No. 25: 3-B(F,F)2BB(F,F)—OCF$_3$
Compound No. 26: 4-B(F,F)2BB(F)—OCF$_3$
Compound No. 27: 4-B(F,F)2BB—OCF$_3$
Compound No. 28: 5-B(F,F)2BB(F,F)—OCF$_2$H
Compound No. 29: 5-B(F,F)2BB(F)—OCF$_2$H
Compound No. 30: 1O5—B(F,F) 2BB—OCF$_2$H
Compound No. 31: 2-B(F,F)2BB(F,F)—CF$_3$
Compound No. 32: 3-B(F,F)2BB(F)—CF$_3$
Compound No. 33: 2-B(F,F)2BB(F)—CF$_2$H
Compound No. 34: 3-B(F,F)2BB—CF$_2$H
Compound No. 35: 4-B(F,F)2BB(F,F)—CFH$_2$
Compound No. 36: 5-B(F)2B(F)B(F,F)—F
Compound No. 37: 7-B(F)2B(F)B—F
Compound No. 38: 8-B(F)2B(F)B(F,F)—CL
Compound No. 39: 5-B(F)2B(F)B—CL
Compound No. 40: 4-B(F)2B(F)B(F,F)—OCF$_3$
Compound No. 41: 3-B(F)2B(F)B—OCF$_3$
Compound No. 42: 1O5-B(F)2B(F)B(F,F)—OCF$_2$H
Compound No. 43: 5-B(F)2B(F)B—OCF$_2$H
Compound No. 44: 3-B(F)2B(F)B(F,F)—CF$_3$
Compound No. 45: 4-B(F)2B(F)B—CF$_3$
Compound No. 46: 2-B(F)2B(F)B(F,F)—CF$_2$H
Compound No. 47: 5-B(F)2B(F)B—CF$_2$H Compound No. 48: 3-B(F)2B(F)B(F,F)—CFH$_2$
Compound No. 49: 3-B2B(F,F)B(F,F)—OCF$_3$
Δε: 13.6, Δn: 0.127, η: 27.0
Compound No. 50: 4-B2B(F,F)B(F)—OCF$_3$
Compound No. 51: 3-B2B(F,F)B(F,F)—OCF$_2$H
Compound No. 52: 3-B2B(F,F)B(F)—OCF$_2$H
Compound No. 53: 5-B2B(F,F)B(F,F)—CF$_3$
Compound No. 54: 2-B2B(F,F)B(F,F)—CF$_2$H
Compound No. 55: 2-B(F,F)2B(F)B(F)—F
Compound No. 56: 4-B(F,F)2B(F)B—F
Compound No. 57: 6-B(F,F)2B(F)B(F,F)—CL
Compound No. 58: 5-B(F,F)2B(F)B(F)—CL
Compound No. 59: 3-B(F,F)2B(F)B(F)—OCF$_3$
Compound No. 60: 1-B(F,F)2B(F)B—OCF$_3$
Compound No. 61: 4O—B(F,F)2B(F)B(F)—OCF$_2$H
Compound No. 62: 9O5-B(F,F)2B(F)B—OCF$_2$H
Compound No. 63: 3-B(F,F)2B(F)B(F)—CF$_3$
Δε: 14.2, Δn: 0.127, η: 28.9
Compound No. 64: 5-B(F,F)2B(F)B—CF$_3$
Compound No. 65: 2-B(F,F)2B(F)B(F)—CF$_2$H
Compound No. 66: 4-B(F,F)2B(F)B—CF$_2$H
Compound No. 67: 3-B(F,F)2B(F)B(F,F)—CFH$_2$
Compound No. 68: 3-B(F)2B(F,F)B(F)—F
Δε: 12.4, Δn: 0.132, η: 31.6
Compound No. 69: 5-B(F)2B(F,F)B—F
Compound No. 70: 5-B(F)2B(F,F)B(F,F)—CL
Compound No. 71: 3-B(F)2B(F,F)B(F)—CL
Δε: 12.5, Δn: 0.139, η: 32.6
Compound No. 72: 4-B(F)2B(F,F)B—CL
Compound No. 73: 2-B(F)2B(F,F)B(F,F)—OCF$_3$
Compound No. 74: 1-B(F)2B(F,F)B(F)—OCF$_3$
Compound No. 75: 6-B(F)2B(F,F)B—OCF$_3$
Compound No. 76: 3-B(F)2B(F,F)B(F,F)—OCF$_2$H
Compound No. 77: 3-B(F)2B(F,F)B(F)—OCF$_2$H
Compound No. 78: 7-B(F)2B(F,F)B—OCF$_2$H
Compound No. 79: 4-B(F)2B(F,F)B(F,F)—CF$_3$
Compound No. 80: 5-B(F)2B(F,F)B(F)—CF$_3$
Compound No. 81: 5-B(F)2B(F,F)B—CF$_3$
Compound No. 82: 4-B(F)2B(F,F)B(F,F)—CF$_2$H
Compound No. 83: 3-B(F)2B(F,F)B(F)—CF$_2$H
Compound No. 84: 3-B(F)2B(F,F)B—CF$_2$H
Compound No. 85: 2-B(F)2B(F,F)B(F)—CFH$_2$
Compound No. 86: 5-B(F,F)2B(F,F)B(F)—F
Compound No. 87: 5O1-B(F,F)2B(F,F)B—F
Compound No. 88: 3-B(F,F)2B(F,F)B(F,F)—CL
Compound No. 89: 4-B(F,F)2B(F,F)B(F)—CL
Compound No. 90: 4-B(F,F)2B(F,F)B(F)—OCF$_3$
Compound No. 91: 5-B(F,F)2B(F,F)B—OCF$_3$
Compound No. 92: 3-B(F,F)2B(F,F)B(F)—OCF$_2$H
Compound No. 93: 2-B(F,F)2B(F,F)B—OCF$_2$H
Compound No. 94: 2-B(F,F)2B(F,F)B(F)—CF$_3$
Compound No. 95: 5-B(F,F)2B(F,F)B(F)—CF$_2$H
Compound No. 96: 5-B(F,F)2B(F,F)B(F,F)—CF$_2$H
Compound No. 97: 3-B(F)4BB(F,F)—F
Compound No. 98: 4-B(F)4BB(F)—OCF$_3$
Compound No. 99: 5-B4B(F)B(F)—CL
Compound No. 100: 4-B4B(F)B(F,F)—CF$_3$
Compound No. 101: 5-B(F,F)4BB(F)—OCF$_3$
Compound No. 102: 3-B(F,F)4BB(F,F)—OCF$_2$H
Compound No. 103: 4-B(F)4B(F)B(F)—F
Compound No. 104: 2-B(F)4B(F)B(F)—CF$_3$
Compound No. 105: 3-B4B(F)B(F,F)—F
Compound No. 106: 5-B4B(F,F)B(F)—CF$_3$
Compound No. 107: 2-B(F,F)4B(F)B(F,F)—F
Compound No. 108: 4-B(F,F)4B(F)B(F)—CF$_2$H
Compound No. 109: 1-B(F)4B(F,F)B(F,F)—F
Compound No. 110: 7-B(F)4B(F,F)B(F)—OCF$_3$
Compound No. 111: 6-B(F,F)4B(F,F)B(F,F)—OCF$_3$
Compound No. 112: 3-B(F,F)4B(F,F)B(F)—CF$_3$
Compound No. 113: 4-B(F)2B(F)2B(F,F)—OCF$_3$
Compound No. 114: 5-B(F)2B(F,F)2B(F,F)—F Embodiment 4

Synthesis of 4'-propyl-3,5-difluoro-4-(2-(3-fluoro-4-chlorophenyl)ethyl)biphenyl (compound (No. 115) represented by general formula (1), where R is $C_3H_7$, each of $Y_3$, $Y_4$, and $Y_5$ is F, X is Cl, $Z_1$ is a covalent bond, and $Z_2$ is —(CH$_2$)$_2$—)

(Step 1) Synthesis of 4'-propyl-3,5-difluoro-4-(2-(3-fluoro-4-chlorophenyl)-1-hydroxyethyl)biphenyl Into a solution of 6.0 g (25.8 mmol) of 4'-propyl-3,5-difluorobiphenyl dissolved in 30 ml of THF, 27 ml (43.9 mmol) of n-BuLi was added dropwise at a speed that maintains a temperature of −60° C. or below, and after completion of addition, the solution was stirred for 1 hour at the same temperature. Then, a solution of 7.2 g (45.2 mmol) of (3-fluoro-4-chlorophenyl)acetaldehyde dissolved in 35 ml of THF was added dropwise at a speed that maintains a temperature of −60° C. or below, and the solution was stirred for 1 hour at the same temperature.

After dropwise addition 100 ml of 1N-HCl into the reaction solution, the solution was extracted with 150 ml of ethyl acetate. The obtained organic layer was washed three times with diluted NaHCO$_3$ solution and three times with water, and dried over anhydrous magnesium sulfate. The solvent was distilled off under reduced pressure, and the residue was subjected to a silica gel column chromatograph (eluent: heptane/ethyl acetate) to obtain 3.7 g of crude 4'-propyl-3,5-difluoro-4-(2-(3-fluoro-4-chlorophenyl)-1-hydroxyethyl)biphenyl (yield: 35.6%).

(Step 2) Synthesis of 4'-propyl-3,5-difluoro-4-(2-(3-fluoro-4-chlorophenyl)ethyl)biphenyl Into the solution of 3.7 g (9.1 mmol) of 4'-propyl-3,5-difluoro-4-(2-(3-fluoro-4-chlorophenyl)-1-hydroxyethyl) biphenyl obtained in the previous step, 18 ml of 1M-CH$_2$Cl$_2$ solution of titanium tetrachloride, and 20 ml of CH$_2$Cl$_2$, 1.6 g (13.7 mmol) of triethylsilane were added dropwise while cooling with ice, and stirred for 3 hours at room temperature. The solution was poured into 100 ml of ice water and extracted by 50 ml of CH$_2$Cl$_2$, and the obtained organic layer was washed twice with a diluted NaHCO$_3$ solution and three times with water, and dried over anhydrous magnesium sulfate. The solvent was distilled off under reduced pressure, and the residue was subjected to a silica gel column chromatograph (eluent: heptane) to obtain 2.8 g of crude 4'-propyl-3,5-difluoro-4-(2-(3-fluoro-4-chlorophenyl)ethyl) biphenyl. The product was recrystallized from a heptane/ethyl acetate (9/1) mixed solution to form 1.7 g of the desired compound (yield: 48.5%).

The transition temperature of this compound was: C 94.1–95.0 Iso

All spectrum data well support its structure. Mass spectrometry: 388(M$^+$)

$^1$H-NMR (CDCl$_3$, TMS internal standard) δ (ppm) 0.96 (t, 3H) 1.53–1.79 (m, 2H) 2.63 (t, 2H) 2.91 (s, 4H) 6.86–7.50 (m, 9H)

Embodiment 5 (Use Example 3)

The properties of liquid crystal composition (C) consisting of 85% composition (A) described above and 15% 4'-propyl-3,5-difluoro-4-(2-(3-fluoro-4-chlorophenyl)ethyl) biphenyl (compound No. 115) obtained in Embodiment 4 are as follows:

NI: 64.7, Δε: 11.7, Δn: 0.142, η: 31.0, Vth: 1.60

Although this liquid crystal composition (C) was stored in a freezer of a temperature of −20° C., neither appearance of a smectic phase nor deposition of crystals was observed even after 60 days.

Embodiment 6 (Use Example 4)

The following compounds can be synthesized according to the method of Embodiment 4. Properties shown here were measured in the same manner as in Embodiment 2.

Compound No. 116: 3-B(F)B2B(F)—OCF$_3$
Compound No. 117: 3-B(F)B2B(F)—OCF$_2$H
Compound No. 118: 3-B(F)B2B(F)—CF$_2$H
Compound No. 119: 3O—B(F)B2B(F,F)—CFH$_2$
Compound No. 120: 1-BB(F)2B(F,F)—F
Compound No. 121: 5-BB(F)2B—F
Compound No. 122: 2-BB(F)2B(F,F)—CL
Compound No. 123: 3-BB(F)2B—CL
Compound No. 124: 5-BB(F)2B(F,F)—OCF$_3$
Compound No. 125: 6-BB(F)2B—OCF$_3$
Compound No. 126: 4-BB(F)2B(F,F)—OCF$_2$H
Compound No. 127: 3-BB(F)2B—OCF$_2$H
Compound No. 128: 5-BB(F)2B(F,F)—CF$_3$
Compound No. 129: 4-BB(F)2B—CF$_3$
Compound No. 130: 3-BB(F)2B(F,F)—CF$_2$H
Compound No. 131: 4-BB(F)2B—CF$_2$H
Compound No. 132: 5-BB(F)2B(F)—CFH$_2$
Compound No. 133: 1-B(F,F)B2B(F,F)—F
Compound No. 134: 2-B(F,F)B2B(F)—F
Compound No. 135: 3-B(F,F)B2B—F
Compound No. 136: 4-B(F,F)B2B(F,F)—CL
Compound No. 137: 5-B(F,F)B2B(F)—CL
Compound No. 138: 7-B(F,F)B2B—CL
Compound No. 139: 2-B(F,F)B2B(F,F)—OCF$_3$
Compound No. 140: 4-B(F,F)B2B(F)—OCF$_3$
Compound No. 141: 16-B(F,F)B2B—OCF$_3$
Compound No. 142: 3-B(F,F)B2B(F,F)—OCF$_2$H
Compound No. 143: 2-B(F. F)B2B(F)—OCF$_2$H
Compound No. 144: 5-B(F,F)B2B—OCF$_2$H
Compound No. 145: 5-B(F,F)B2B(F,F)—CF,
Compound No. 146: 4-B(F,F)B2B(F)—CF$_3$
Compound No. 147: 3-B(F,F)B2B—CF$_3$
Compound No. 148: 3-B(F,F)B2B(F,F)—CF$_2$H
Compound No. 149: 1O1-B(F,F)B2B(F)—CF$_2$H
Compound No. 150: 5-B(F,F)B2BF—CF$_2$H
Compound No. 151: 6-B(F,F)B2B(F)—CFH$_2$
Compound No. 152: 2-B(F)B(F)2B(F,F)—F
Compound No. 153: 5-B(F)B(F)2B—F
Compound No. 154: 2-B(F)B(F)2B(F,F)—CL
Compound No. 155: 4-B(F)B(F)2B—CL
Compound No. 156: 3-B(F)B(F)2B(F,F)—OCF$_3$
Compound No. 157: 3-B(F)B(F)2B—OCF$_3$
Compound No. 158: 3-B(F)B(F)2B(F,F)—OCF$_2$H
Compound No. 159: 5-B(F)B(F)2B(F,F)—CF$_3$
Compound No. 160: 2-B(F)B(F)2B—CF$_3$
Compound No. 161: 5-B(F)B(F)2B(F,F)—CF$_2$H
Compound No. 162: 5-B(F)B(F)2B—CF$_2$H
Compound No. 163: 4-B(F)B(F)2B(F,F)—CFH$_2$
Compound No. 164: 5-BB(F,F)2B(F)—F
Compound No. 165: 6-BB(F,F)2B—F
Compound No. 166: 1-BB(F,F)2B(F)—CL
Compound No. 167: 7-BB(F,F)2B—CL
Compound No. 168: 4-BB(F,F)2B(F)—OCF$_3$
Compound No. 169: 2-BB(F,F)2B—OCF$_3$
Compound No. 170: 2-BB(F,F)2B(F)—OCF$_2$H
Compound No. 171: 5-BB(F,F)2B—OCF$_2$H
Compound No. 172: 3-BB(F,F)2B(F,F)—CF$_3$
Compound No. 173: 3-BB(F,F)2B(F)—CF$_3$
Compound No. 174: 5O1-BB(F,F)2B—CF$_3$
Compound No. 175: 4-BB(F,F)2B(F)—CF$_2$H
Compound No. 176: 6-BB(F,F)2B—CF$_2$H
Compound No. 177: 2-BB(F,F)2B(F,F)—CFH$_2$
Compound No. 178: 3-B(F,F)B(F)2B(F,F)—F
Compound No. 179: 3-B(F,F)B(F)2B(F)—F
Compound No. 180: 3-B(F,F)B(F)2B—F
Compound No. 181: 3-B(F,F)B(F)2B(F,F)—CL
Δε: 12.6, Δn: 0.135, η: 28.6
Compound No. 182: 3-B(F,F)B(F)2B(F)—CL
Compound No. 183: 3-B(F,F)B(F)2B—CL
Compound No. 184: 3-B(F,F)B(F)2B(F,F)—OCF$_3$
Compound No. 185: 3B(F,F)B(F)2B(F)—OCF$_3$
Compound No. 186: 3B(F,F)B(F)2B—OCF$_3$
Compound No. 187: 3-B(F,F)B(F)2B(F,F)—OCF$_2$H
Compound No. 188: 5-B(F,F)B(F)2B(F)—OCF$_2$H
Compound No. 189: 5-B(F,F)B(F)2B—F OCF$_2$H
Compound No. 190: 3-B(F,F)B(F)2B(F,F)—CF$_3$
Δε: 14.9, Δn: 0.124, η: 27.4
Compound No. 191: 5-B(F,F)B(F)2B(F)—CF$_3$
Compound No. 192: 5-B(F,F)B(F)2B—CF$_3$
Compound No. 193: 3-B(F,F)B(F)2B(F,F)—CFH$_2$
Compound No. 194: 5-B(F,F)B(F)2B(F)—CF$_2$H
Compound No. 195: 5-B(F,F)B(F)2B—CF$_2$H
Compound No. 196: 5-B(F,F)B(F)2B(F)—CFH$_2$
Compound No. 197: 3O3-B(F)B(F,F)2B(F)—F
Compound No. 198: 4-B(F)B(F,F)2B—F
Compound No. 199: 5-B(F)B(F,F)2B(F)—CL
Compound No. 200: 17-B(F)B(F,F)2B—CL
Compound No. 201: 2-B(F)B(F,F)2B(F)—OCF$_3$
Compound No. 202: 1-B(F)B(F,F)2B—OCF$_3$
Compound No. 203: 3-B(F)B(F,F)2B(F)—OCF$_2$H
Compound No. 204: 4-B(F)B(F,F)2B—OCF$_2$H
Compound No. 205: 3-B(F)B(F,F)2B(F)—CF$_3$
Δε: 13.9, Δn: 0.127, η: 27.7
Compound No. 206: 5-B(F)B(F,F)2B—CF$_3$
Compound No. 207: 1O—B(F)B(F,F)2B(F)—CF$_2$H
Compound No. 208: 6-B(F)B(F,F)2B—CF$_2$H
Compound No. 209: 7-B(F)B(F,F)2B(F,F)—CFH$_2$
Compound No. 210: 3-B(F,F)B(F,F)2B(F)—F
Compound No. 211: 3-B(F,F)B(F,F)2B—F
Compound No. 212: 3-B(F,F)B(F,F)2B(F)—CL
Compound No. 213: 4-B(F,F)B(F,F)2B—CL
Compound No. 214: 4-B(F,F)B(F,F)2B(F)—O CF$_3$
Compound No. 215: 4-B(F,F)B(F,F)2B—OCF$_3$
Compound No. 216: 5-B(F,F)B(F,F)2B(F)—OCF$_2$H
Compound No. 217: 5-B(F,F)B(F,F)2B—OCF$_2$H
Compound No. 218: 5-B(F,F)B(F,F)2B(F)—CF$_3$
Compound No. 219: 2-B(F,F)B(F,F)2B—CF$_3$
Compound No. 220: 4-B(F,F)B(F,F)2B(F)—CF$_2$H
Compound No. 221: 6-B(F,F)B(F,F)2B—CF$_2$H
Compound No. 222: 4-B(F,F)B(F,F)2B(F)—CFH$_2$
Compound No. 223: 5-B(F)B4B(F,F)—F
Compound No. 224: 5-B(F)B4B(F)—CL
Compound No. 225: 3-B(F)B4B(F,F)—OCF$_3$
Compound No. 226: 2-B(F)B4B(F)—CF$_3$
Compound No. 227: 3-BB(F)4B(F)—F
Compound No. 228: 4-BB(F)4B(F)—OCF$_3$
Compound No. 229: 6-B(F,F)B4B(F,F)—CF$_3$
Compound No. 230: 5-B(F,F)B4B(F)—OCF$_2$H
Compound No. 231: 9-B(F)B(F)4B(F)—OCF$_3$
Compound No. 232: 2-B(F)B(F)4B(F)—CF$_3$
Compound No. 233: 3-BB(F,F)4B(F,F)—F
Compound No. 234: 1-BB(F,F)4B(F,F)—CL
Compound No. 235: 7-B(F,F)B(F)4B—F
Compound No. 236: 6-B(F,F)B(F)4B—OCF$_3$
Compound No. 237: 5-B(F)B(F,F)4B(F,F)—OCF$_3$
Compound No. 238: 4-B(F)B(F,F)4B(F,F)—CF$_3$
Compound No. 239: 3-B(F,F)B(F,F)4B(F,F)—F
Compound No. 240: 2-B(F,F)B(F,F)4B(F,F)—CL Embodiment 7

Synthesis of (2'-fluoro-4'-propyl-3-fluorobiphenyl-4-yl)methyl=3,4-difluorophenyl=ether (compound (No. 241) represented by general formula (1), where R is $C_3H_7$, each of $Y_1$, $Y_3$, and $Y_5$ is F, X is F, $Z_1$ is a covalent bond, and $Z_2$ is —$CH_2O$—)

Into the mixture of 0.6 g (13.8 mmol) of NaH and 3 ml of dimethyl formamide (DMF), a solution of 1.8 g (13.8 mmol) of 3,4-difluorophenol dissolved in 20 ml of DMF was added dropwise, and the mixture was stirred for 1 hour. Into this mixture, 3.0 g (9.2 mmol) of 2'-fluoro-4'-propyl-3-fluoro-4-bromomethylbiphenyl was added, and the mixture was heated and refluxed for 4 hours. The reaction mixture was poured into 50 ml of 1N-HCl and extracted by 100 ml of ethyl acetate, and the obtained organic layer was washed twice with a diluted $NaHCO_3$ solution and three times with water, and dried over anhydrous magnesium sulfate. The solvent was distilled off under reduced pressure, and the residue was subjected to a silica gel column chromatograph (eluent: heptane) to obtain crude (2'-fluoro-4'-propyl-3-fluorobiphenyl-4-yl)methyl 3,4-difluorophenyl ether.

The product was recrystallized from an ethanol/ethyl acetate (9/1) mixed solvent to form the desired compound.

The following compounds Nos. 242 to 278 can be synthesized in the same manner as in Embodiment 7.
Compound No. 242: 3-B(F)CH$_2$OBB(F,F)—CL
Compound No. 243: 3-B(F)CH$_2$OBB(F,F)—CF$_3$
Compound No. 244: 1O5-BCH$_2$OB(F)B(F)—F
Compound No. 245: 3-BCH$_2$OB(F)B(F,F)—OCF$_2$H
Compound No. 246: 3-B(F,F)CH$_2$OBB(F)—CL
Compound No. 247: 3-B(F,F)CH$_2$OBB(F,F)—OCF$_3$
Compound No. 248: 5O—B(F)CH$_2$OB(F)B(F)—OCF$_3$
Compound No. 249: 3-B(F)CH$_2$OB(F)B(F)—CF$_3$
Compound No. 250: 3-BCH$_2$OB(F,F)B(F,F)—F
Compound No. 251: 3-BCH$_2$OB(F,F)B(F)—CL
Compound No. 252: 5O1-B(F,F)CH$_2$OB(F)B—OCF$_3$
Compound No. 253: 5-B(F,F)CH$_2$OB(F)B(F,F)—CF$_3$
Compound No. 254: 5-B(F)CH$_2$OB(F,F)B(F,F)—F
Compound No. 255: 5-B(F)CH$_2$OB(F,F)B(F)—OCF$_2$H
Compound No. 256: 5-B(F,F)CH$_2$OB(F,F)B—F
Compound No. 257: 5-B(F,F)CH$_2$OB(F,F)B(F,F)—OCF$_3$
Compound No. 258: 5-B(F,F)OCH$_2$B(F)B(F)—F
Compound No. 259: 3-B(F)BCH$_2$OB(F,F)—F
Compound No. 260: 5-B(F)BCH$_2$OB(F)—CL
Compound No. 261: 3-BB(F)CH$_2$OB(F)—OCF$_3$
Compound No. 262: 5-BB(F)CH$_2$OB(F,F)—CF$_2$H
Compound No. 263: 3-B(F,F)BCH$_2$OB(F,F)—CL
Compound No. 264: 5-B(F,F)BCH$_2$OB(F)—CF$_3$
Compound No. 265: 3-B(F)B(F)CH$_2$OB(F)—OCF$_2$H
Compound No. 266: 3-BB(F,F)CH$_2$OB(F,F)—OCF$_3$
Compound No. 267: 5-BB(F,F)CH$_2$OB(F)—CF$_2$H
Compound No. 268: 3O-B(F,F)B(F)CH$_2$OB(F,F)—F
Compound No. 269: 5-B(F,F)B(F)CH$_2$OB—CF$_3$
Compound No. 270: 3O1-B(F)B(F,F)CH$_2$OB(F,F)—CL
Compound No. 271: 3-B(F)B(F,F)CH$_2$OB(F)—CF$_3$
Compound No. 272: 1O3-B(F,F)B(F,F)CH$_2$OB(F,F)—F
Compound No. 273: 5-B(F,F)B(F,F)CH$_2$OB—OCF$_3$
Compound No. 274: 3-BB(F,F)OCH$_2$O(F)—CL
Compound No. 275: 5-B(F)2B(F,F)CH$_2$OB(F)B—OCF$_3$
Compound No. 276: 5-B(F)CH$_2$OB(F)2B(F,F)—CF$_3$
Compound No. 277: 5-B2B(F)OCH$_2$B(F,F)—F
Compound No. 278: 5-B(F)OCH$_2$B(F,F)2B(F)—OCF$_2$H Embodiment 8 (Use Example 5)

The properties of the liquid crystal composition of composition example 1 described above are as follows:

NI: 88.6, Δε: 8.3, Δn: 0.150, η: 20.5, Vth: 1.73

Although this liquid crystal composition was stored in a freezer of a temperature of −20° C., neither appearance of a smectic phase nor deposition of crystals was observed even after 60 days.

Embodiment 9 (Use Example 6)

The properties of the liquid crystal composition of composition example 2 described above are as follows:

NI: 78.7, Δε: 8.5, Δn: 0.152, η: 21.8, Vth: 2.23

Although this liquid crystal composition was stored in a freezer of a temperature of −20° C., neither appearance of a smectic phase nor deposition of crystals was observed even after 60 days.

Embodiment 10 (Use Example 7)

The properties of the liquid crystal composition of composition example 3 described above are as follows:

NI: 90.7, Δε: 29.8, Δn: 0.152, η: 88.0, Vth: 0.94

Although this liquid crystal composition was stored in a freezer of a temperature of −20° C., neither appearance of a smectic phase nor deposition of crystals was observed even after 60 days.

Embodiment 11 (Use Example 8)

The properties of the liquid crystal composition of composition example 4 described above are as follows:

NI: 84.9, Δε: 7.2, Δn: 0.195, η: 36.5, Vth: 1.96

Although this liquid crystal composition was stored in a freezer of a temperature of −20° C., neither appearance of a smectic phase nor deposition of crystals was observed even after 60 days.

Embodiment 12 (Use Example 9)

The properties of the liquid crystal composition of composition example 5 described above were as follows:

NI: 62.6, Δε: 10.2, Δn: 0.119, η: 38.4, Vth: 1.52

Although this liquid crystal composition was stored in a freezer of a temperature of −20° C., neither appearance of a smectic phase nor deposition of crystals was observed even after 60 days.

Embodiment 13 (Use Example 10)

The properties of the liquid crystal composition of composition example 6 described above are as follows:

NI: 72.5, Δε: 9.1, Δn: 0.146, η: 23.3, Vth: 1.35

Although this liquid crystal composition was stored in a freezer of a temperature of −20° C., neither appearance of a smectic phase nor deposition of crystals was observed even after 60 days.

Embodiment 14 (Use Example 11)

The properties of the liquid crystal composition of composition example 7 described above are as follows:

NI: 76.1, Δε: 23.3, Δn: 0.115, η: 34.3, Vth: 1.09

Although this liquid crystal composition was stored in too a freezer of a temperature of −20° C., neither appearance of a smectic phase nor deposition of crystals was observed even after 60 days.

Embodiment 15 (Use Example 12)

The properties of the liquid crystal composition of composition example 8 described above are as follows:

NI: 90.8, Δε: 5.4, Δn: 0.116, η: 17.8, Vth: 2.17

Although this liquid crystal composition was stored in a freezer of a temperature of −20° C., neither appearance of a smectic phase nor deposition of crystals was observed even after 60 days.

Embodiment 16 (Use Example 13)

The properties of the liquid crystal composition of composition example 9 described above are as follows:

NI: 85.6, Δε: 29.0, Δn: 0.143, η: 43.0, Vth: 0.82

Although this liquid crystal composition was stored in a freezer of a temperature of −20° C., neither appearance of a smectic phase nor deposition of crystals was observed even after 60 days.

Embodiment 17 (Use Example 14)

The properties of the liquid crystal composition of composition example 10 described above are as follows:

NI: 57.1, Δε: 9.8, Δn: 0.113, η: 28.7, Vth: 1.51

Although this liquid crystal composition was stored in a freezer of a temperature of −20° C., neither appearance of a smectic phase nor deposition of crystals was observed even after 60 days.

Embodiment 18 (Use Example 15)

The properties of the liquid crystal composition of composition example 11 described above are as follows:

NI: 64.7, Δε: 7.3 Δn: 0.154, η: 23.9, Vth: 1.62

Although this liquid crystal composition was stored in a freezer of a temperature of −20° C., neither appearance of a smectic phase nor deposition of crystals was observed even after 60 days.

Embodiment 19 (Use Example 16)

The properties of the liquid crystal composition of composition example 12 described above are as follows:

NI: 95.1, Δε: 5.8, Δn: 0.092, η: 26.2, Vth: 1.96

Although this liquid crystal composition was stored in a freezer of a temperature of −20° C., neither appearance of a smectic phase nor deposition of crystals was observed even after 60 days.

Embodiment 20 (Use Example 17)

The properties of the liquid crystal composition of composition example 13 described above are as follows:

NI: 81.2, Δε: 4.2, Δn: 0.095, η: 20.4, Vth: 2.38

Although this liquid crystal composition was stored in to a freezer of a temperature of −20° C., neither appearance of a smectic phase nor deposition of crystals was observed even after 60 days.

Embodiment 21 (Example 18)

The properties of the liquid crystal composition of composition example 14 described above are as follows:

NI: 81.8, Δε: 6.2, Δn: 0.115, η: 25.4, Vth: 1.85

Although this liquid crystal composition was stored in a freezer of a temperature of −20° C., neither appearance of a smectic phase nor deposition of crystals was observed even after 60 days.

Embodiment 22 (Use Example 19)

The properties of the liquid crystal composition of composition example 15 described above are as follows:

NI: 67.1, Δε: 9.4, Δn: 0.088, η: 29.2, Vth: 1.38

Although this liquid crystal composition was stored in a freezer of a temperature of −20° C., neither appearance of a smectic phase nor deposition of crystals was observed even after 60 days.

Embodiment 23 (Use Example 20)

The properties of the liquid crystal composition of composition example 16 described above are as follows:

NI: 71.7, Δε: 13.5, Δn: 0.083, η: 35.5, Vth: 1.25

Although this liquid crystal composition was stored in a freezer of a temperature of −20° C., neither appearance of a smectic phase nor deposition of crystals was observed even after 60 days.

Embodiment 24 (Use Example 21)

The properties of the liquid crystal composition of composition example 17 described above are as follows:

NI: 88.3, Δε: 5.4, Δn: 0.128, η: 21.8, Vth: 2.04

Although this liquid crystal composition was stored in a freezer of a temperature of −20° C., neither appearance of a smectic phase nor deposition of crystals was observed even after 60 days.

Embodiment 25 (Use Example 22)

The properties of the liquid crystal composition of composition example 18 described above are as follows:

NI: 90.1, Δε: 10.0, Δn: 0.115, η: 36.9, Vth: 1.41

Although this liquid crystal composition was stored in a freezer of a temperature of −20° C., neither appearance of a smectic phase nor deposition of crystals was observed even after 60 days.

Embodiment 26 (Use Example 23)

The properties of the liquid crystal composition of composition example 19 described above are as follows:

NI: 80.7, Δε: 5.1, Δn: 0.091, η: 15.5, Vth: 2.24

Although this liquid crystal composition was stored in a freezer of a temperature of −20° C., neither appearance of a smectic phase nor deposition of crystals was observed even after 60 days.

Embodiment 27 (Use Example 24)

The properties of the liquid crystal composition of composition example 20 described above are as follows:

NI: 60.1, Δε: 9.4, Δn: 0.094, η: 27.4, Vth: 1.48

Although this liquid crystal composition was stored in a freezer of a temperature of −20° C., neither appearance of a smectic phase nor deposition of crystals was observed even after 60 days.

Embodiment 28 (Use Example 25)

The properties of the liquid crystal composition of composition example 21 described above are as follows:

NI: 88.7, Δε: 8.1, Δn: 0.134, η: 36.6, Vth: 1.68

Although this liquid crystal composition was stored in a freezer of a temperature of −20° C., neither appearance of a smectic phase nor deposition of crystals was observed even after 60 days.

Embodiment 29

Synthesis of 4'-(2-(4-propylphenyl)ethyl)-3,4,5,2'-tetrafluorobiphenyl (compound No. 13)

(The First Step)

Synthesis of (2-(4-propylphenyl)ethyl)-3-fluoro-4-iodobenzene

To a solution of 2.45 g (10.1 mmol) of (2-(4-propylphenyl)ethyl)-3-fluorobenzene in 40 ml of tetrahydrofuran, was added dropwise 11 ml (11.1 mmol) of sec-BuLi with keeping the temperature at −60° C. or lower. After finishing the addition, the solution was stirred for 2 hours at the same temperature. Then, a solution of 2.9 g (11.6 mmol) of iodine in 20 ml of THF was added dropwise to the solution with keeping the temperature at −60° C. or lower. The mixture was stirred for 1 hour at the same temperature.

To the reaction solution was added dropwise 50 ml of 1N-HCl, then the mixture was extracted with 50 ml of heptane. The organic phase was washed three times with a diluted $NaHCO_3$ and three times with water, then dried over anhydrous magnesium sulphate. The solvent was distilled off under reduced pressure, the residue was subjected to a silica gel column chromatograph using heptane as an eluent to obtain 3.3 g of crude (2-(4-propylphenyl)ethyl)-3-fluoro-4-iodobenzene. The yield was 88.3%.

(The Second Step)

Synthesis of 4'-(2-(4-propylphenyl)ethyl)-3,4,5,2'-tetrafluorobiphenyl

Mixed were 3.3 g (8.9 mmol) of (2-(4-propylphenyl) ethyl)-3-fluoro-4-iodobenzene obtained at the previous step, 2.1 g (11.9 mmol) of dihydroxy-(3,4,5-trifluorophenyl) borane, 2.5 g (18.3 mmol) of $K_2CO_3$, 0.3 g of 5% Pd—C and 30 ml of a mixed solvent of toluene/ethanol/water (1/1/1 by volume), and the mixture was heated to reflux for 12 hours. Then, after the Palladium-Carbon was removed by filtration, the mixture was extracted with 100 ml of toluene. The organic phase was washed three times with water and dried over anhydrous magnesium sulphate. The solvent was distilled off under reduced pressure, and the obtained residue was subjected to a silica gel column chromatograph using heptane as an eluent to obtain 2.0 g of crude 4'-(2-(4-propylphenyl)ethyl)-3,4,5,2'-tetrafluorobiphenyl. This crude matter was recrystallized from ethanol to obtain 0.94 g of the purified compound. The yield was 28.3%.

The phase transition temperature of the compound was: C 60.3–60.8 ISO

All spectrum data well support its structure. Mass spectrometry: 372(M$^+$)

$^1$H-NMR (CDCl$_3$, TMS internal standard) δ (ppm) 0.96 (t, 3H) 1.66 (m, 2H) 2.55 (t, 2H) 2.88 (m, 4H) 6.89–7.41 (m, 9H)

Embodiment 30 (Use Example 26)

The physical properties of the liquid crystal composition (D) comprising 85% by weight of the above composition (A) and 15% by weight of 4'-(2-(4-propylphenyl)ethyl)-3,4,5,2'-tetrafluorobiphenyl (compound No. 13) obtained in Embodiment 29 are as follows:

NI: 60.3, Δε: 12.1, Δn: 0.133, η: 30.5, Vth: 1.48, τ: 285

This liquid crystal composition (D) was left to stand in a freezer at −20° C. for 60 days or more, but smectic phase did not appear and precipitation of crystal was not found.

Comparative Embodiment 1

The following are the physical properties of the liquid crystal composition (E) comprising 85% by weight of the above composition (A) and 15% by weight of [4-(2-(4-propylphenyl)ethyl)-2,6,3',4'-tetrafluorobiphenyl] described on page 15 of JP6-504032 as a comparative compound:

NI: 59.0, Δε: 12.1, Δn: 0.133, η: 32.0, Vth: 1.64, τ: 354

This liquid crystal composition (E) was left to stand in a freezer at −20° C. for 60 days or more, but smectic phase did not appear and precipitation of crystal was not found.

INDUSTRIAL APPLICABILITY

The liquid crystalline compounds of the present invention have high voltage holding ratios which have a very small degree of temperature dependence, low threshold voltages which have a very small degree of temperature dependence, high Δn values, and good solubility to other liquid crystal materials even at low temperature. By appropriate selection the substituents and bonding groups of the liquid crystalline compounds of the present invention, a novel liquid crystalline compound having desired properties can be provided.

Therefore, by use of the liquid crystalline compounds of the present invention, there can be provided a novel liquid crystal composition having an extremely high voltage holding ratio which has a very small degree of temperature dependence, low threshold voltages, adequately high Δn and Δε values, and excellent miscibility with other liquid crystal materials. Also, an excellent liquid crystal display element can be provided by use of such a liquid crystal composition.

Specifically, in comparison of Embodiment 30 with Comparative Embodiment 1, the compound of the present invention can serve to reduce the response time by approximately 20% (354 ms to 285 ms). It has not been known that such a remarkable effect is brought about owing to a different position of substituted fluorine atoms. This finding proves an unobviousness of the present invention.

What is claimed is:

1. A substituted benzene derivative represented by general formula (100),

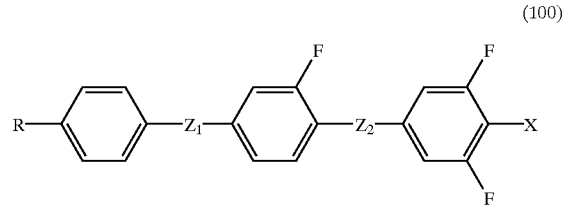

(100)

where, R represents a straight chain or branched alkyl group having 1 to 20 carbon atoms, in which each of optional and nonadjacent methylene group (—CH$_2$—) may be substituted by an oxygen atom; X represents a halogen atom, —CF$_3$, —CF$_2$H, —CFH$_2$, —OCF$_3$ or —OCF$_2$H; each of Z$_1$ and Z$_2$ independently represents —(CH$_2$)$_2$—, —(CH$_2$)$_4$—, —CH$_2$O—, —OCH$_2$— or a covalent bond, but when Z$_1$ represents (CH$_2$)$_2$— or a covalent bond, Z$_2$ cannot be a covalent bond.

2. A substituted benzene derivative according to claim 1, wherein Z$_1$=a covalent bond and Z$_2$=—(CH$_2$)$_2$—.

3. A substituted benzene derivative according to claim 1, wherein Z$_1$=—(CH$_2$)$_4$—, —CH$_2$O—, or —OCH$_2$— and Z$_2$=a covalent bond.

4. A substituted benzene derivative according to claim 1, wherein Z$_1$=a covalent bond, and Z$_2$=—(CH$_2$)$_4$—, —CH$_2$O— or —OCH$_2$—.

5. A substituted benzene derivative according to claim 1, wherein Z$_1$=Z$_2$=—(CH$_2$)$_2$—.

6. A liquid crystal composition containing at least one compound according to any one of claims 1–5.

7. A liquid crystal composition containing at least one compound according to any one of claims 1–5 as a first component, and at least one compound selected from a group consisting of compounds represented by the following general formulas (2), (3) and (4) as a second component,

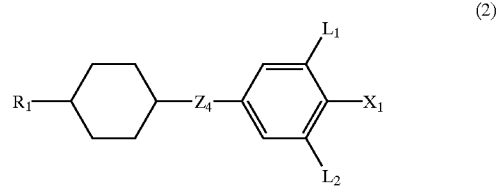

(2)

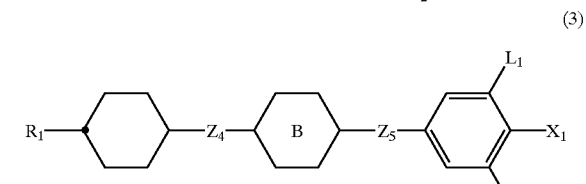

(3)

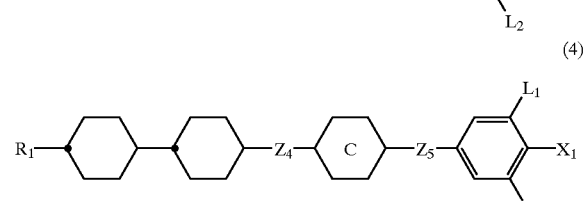

(4)

where, R$_1$ represents an alkyl group having 1 to 10 carbon atoms in which each of optional and nonadjacent methylene groups may be substituted by an oxygen atoms or —CH=CH—, and optional hydrogen atoms may be substituted by fluorine atoms; $X_1$ represents a fluorine atom, a chlorine atom, —$OCF_3$, —$OCF_2H$, —$CF_3$, —$CF_2H$, —$CFH_2$, —$OCF_2CF_2H$ or —$OCF_2CFHCF_3$; each of $L_1$ and $L_2$ independently represents a hydrogen atom or a fluorine atom; each of $Z_4$ and $Z_5$ independently represents a 1,2-ethylene group, a 1,4-butylene group, —COO—, —$CF_2O$—, —$OCF_2$—, —CH=CH— or a covalent bond; ring B represents trans-1,4-cyclohexylene, 1,3-dioxane-2,5-diyl, or 1,4-phenylene in which hydrogen atoms may be substituted by fluorine atoms; ring C represents trans-1,4-cyclohexylene, or 1,4-phenylene in which hydrogen atoms may be substituted by fluorine atoms.

8. A liquid crystal composition containing at least one compound according to any one of claims 1–5 as a first component, and at least one compound selected from a group consisting of compounds represented by the following general formulas (5) and (6) as a second component,

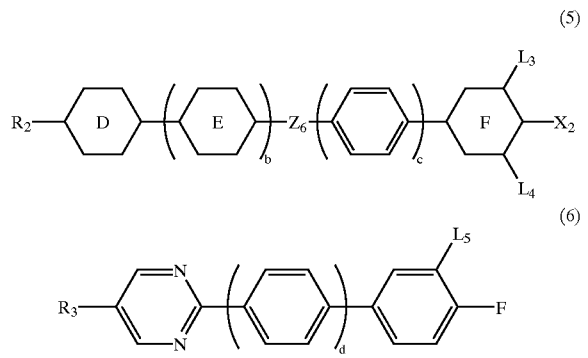

(5)

(6)

where, each of $R_2$ and $R_3$ independently represents an alkyl group having 1 to 10 carbon atoms in which each of optional and nonadjacent methylene groups may be substituted by an oxygen atoms or —CH=CH—, and optional hydrogen atoms may be substituted by fluorine atoms; $X_2$ represents a —CN group or —C≡C—CN; ring D represents trans-1,4-cyclohexylene, 1,4-phenylene, 1,3-dioxane-2,5-diyl or pyrimidine-2,5-diyl; ring E represents trans-1,4-cyclohexylene, 1,4-phenylene in which hydrogen atoms may be substituted by fluorine atoms or pyrimidine-2,5-diyl; ring F represents trans-1,4-cyclohexylene or 1,4-phenylene; $Z_6$ represents a 1,2-ethylene group, —COO— or a covalent bond; each of $L_3$, $L_4$, and $L_5$ independently represents a hydrogen atoms or a fluorine atom; each of b, c and d independently represents 0 or 1.

9. A liquid crystal composition containing at least one compound according to any one of claims 1–5 as a first component, at least one compound selected from a group consisting of compounds represented by the above general formulas (2), (3) and (4) as a second component,

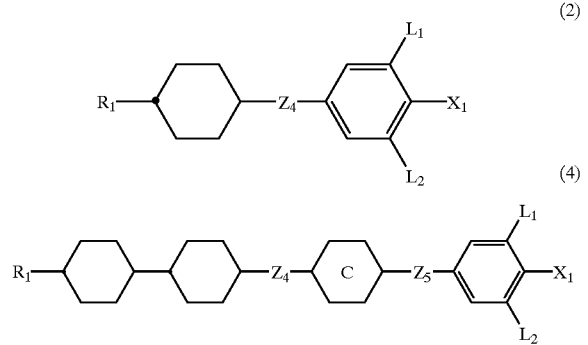

(2)

(4)

where, $R_1$ represents an alkyl group having 1 to 10 carbon atoms in which each of optional and nonadjacent methylene groups may be substituted by an oxygen atom or —CH=CH—, and optional hydrogen atoms may be substituted by fluorine atoms; $X_1$ represents a fluorine atom, a chlorine atom, —$OCF_3$, —$OCF_2H$, —$CF_3$, —$CF_2H$, —$CFH_2$, —$OCF_2CF_2H$ or —$OCF_2CFHCF_3$; each of $L_1$ and $L_2$ independently represents a hydrogen atom or a fluorine atom; each of $Z_4$ and $Z_5$ independently represents a 1,2-ethylene group, a 1,4-butylene group, —COO—, —$CF_2O$—, —$OCF_2$—, —CH=CH— or a covalent bond; ring B represents trans-1,4-cyclohexylene, 1,3-dioxane-2,5-diyl, or 1,4-phenylene in which hydrogen atoms may be substituted by fluorine atoms; ring C represents trans-1,4-cyclohexylene, or 1,4-phenylene and at least one compound selected from a group consisting of compounds represented by the following general formulas

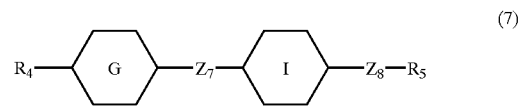

(7)

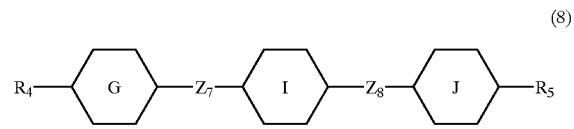

(8)

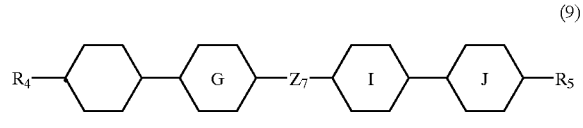

(9)

where, each of $R_4$ and $R_5$ independently represents an alkyl group having 1 to 10 carbon atoms in which each of optional and nonadjacent methylene groups may be substituted by an oxygen atom or —CH=CH—, and optional hydrogen atoms may be substituted by fluorine atoms; each of ring G, ring I and ring J independently represents trans-1,4-cyclohexylene, pyrimidine-2,5-diyl, or 1,4-phenylene in which hydrogen atoms may be substituted by fluorine atoms; each of $Z_7$ and $Z_8$ independently represents —C≡C—, —COO—, —$CH_2CH_2$—, —CH=CH— or a covalent bond.

10. A liquid crystal composition containing at least one compound according to any one of claims 1–5 as a first component, at least one compound selected from a group

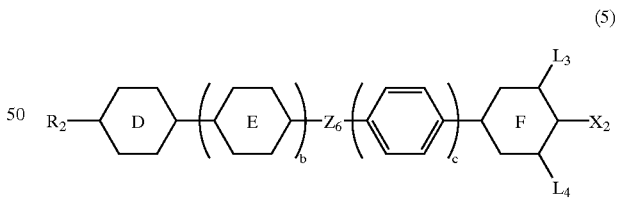

(5)

(6)

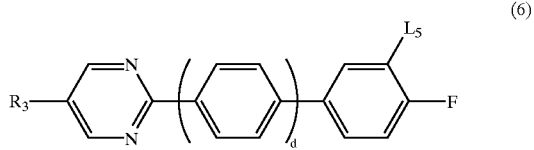

where, each of $R_2$ and $R_3$ independently represents an alkyl group having 1 to 10 carbon atoms in which each of optional and nonadjacent methylene groups may be substituted by an oxygen atom or —CH=CH—, and optional hydrogen atoms may be substituted by an oxygen atom or —CH=CH—, and optional hydrogen atoms may be substituted by fluorine atoms; $X_2$ represents a —CN group or —C≡C—CN; ring D represents trans-1,4-cyclohxylene, 1,4-phenylene, 1,3-dioxane-2,5-diyl or pyrimidine-2,5-diyl; ring E represents trans-1,4-cyclohexylene, 1,4-phenylene in which hydrogen atoms may be substituted by fluorine atoms or pyrimidine-2,5-diyl; ring F represents trans-1,4-cyclohexylene or 1,4-phenylene; $Z_6$ represents a 1,2-ethylene group, —COO— or a covalent bond; each of $L_3$, $L_4$, and $L_5$ independently represents a hydrogen atom or a fluorine atom; each of b, c and d independently represents 0 or 1,

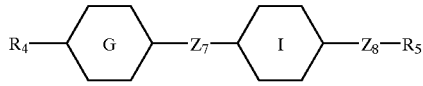

(7)

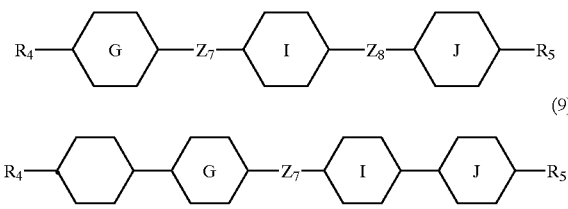

(8)

(9)

where, each of $R_4$ and $R_5$ independently represents an alkyl group having 1 to 10 carbon atoms in which each of optional and nonadjacent methylene groups may be substituted by an oxygen atom or —CH=CH—, and optional hydrogen atoms may be substituted by fluorine atoms; each of ring G, ring I and ring J independently represents trans-1,4-cyclohexylene, pyrimidine-2,5-diyl, or 1,4-phenylene in which hydrogen atoms may be substituted by fluorine atoms; each of $Z_7$ and $Z_8$ independently represents —C≡C—, —COO—, —CH$_2$CH$_2$—, —CH=CH— or a covalent bond.

11. A liquid crystal composition containing at least one compound according to any one of claims 1–5 as a first component, at least one compound selected from a group consisting of compounds represented by the following general formulas (5) and (6) as a second component,

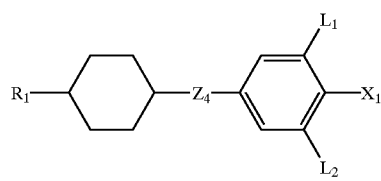

(2)

(3)

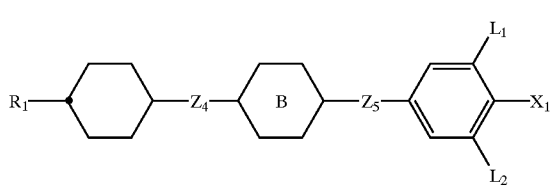

(4)

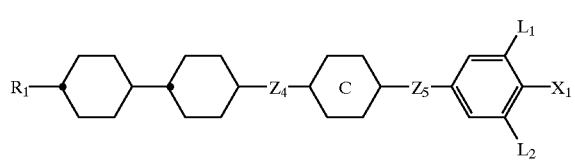

where, $R_1$ represents an alkyl group having 1 to 10 carbon atoms in which each of optional nonadjacent methylene groups may be substituted by an oxygen atom or —CH=CH—, and optional hydrogen atoms may be substituted by fluorine atoms; $X_1$ represents a fluorine atom, a chlorine atoms, —OCF$_3$, —OCF$_2$H, —CF$_3$, —CF$_2$H, —CFH$_2$, —OCF$_2$CF$_2$H or —OCF$_2$CFHCF$_3$; each of $L_1$ and $L_2$ independently represents a hydrogen atom or a fluorine atom; each of $Z_4$ and $Z_5$ independently represents a 1,2-ethylene group, a 1,4-butylene group, —COO—, CF$_2$O—, —OCF—, —CH=CH or a covalent bond; ring B represents trans-1,4-cyclohexylene, 1,3-dioxane-2,5-diyl, or 1,4-phenylene in which hydrogen atoms may be substituted by fluorine atoms; ring C represents trans-1,4-cyclohexylene, or 1,4-phenylene in which hydrogen atoms may be substituted by fluorine atoms, at least one compound selected from a group consisting of compounds represented by the above general formulas (5) and (6) as a third component,

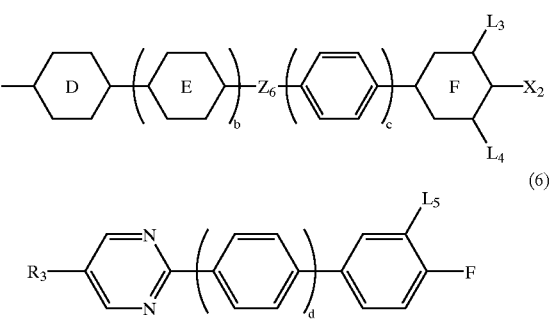

(5)

(6)

where, each of $R_2$ and $R_3$ independently represents an alkyl group having 1 to 10 carbon atoms in which each of optional and nonadjacent methylene groups may be substituted by an oxygen atoms or —CH=CH—, and optional hydrogen atoms may be substituted by fluorine atoms; $X_2$ represents a —CN group or —C≡C—CN; ring D represents trans-1,4-cyclohexylene, 1,4-phenylene, 1,3-dioxane-2,5-diyl or pyrimidine-2,5-diyl; ring E represents trans-1,4-cyclohexylene, 1,4-phenylene in which hydrogen atoms may be substituted by fluorine atoms or pyrimidine-2,5-diyl; ring F represents trans-1,4-cyclohexylene or 1,4-phenylene; $Z_6$ represents a 1,2-ethylene group, —COO— or a covalent bond; each of $L_3$, $L_4$, and $L_5$ independently represents a hydrogen atom or a fluorine atom; each of b, c and d independently represents 0 or 1, and at least one compound selected from a group consisting of compounds represented by the following general formulas (7), (8), and (9) as a fourth component,

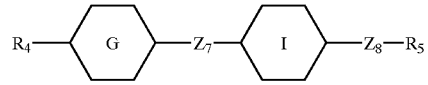

(7)

(8)

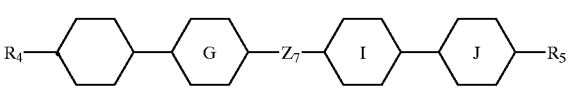

(9)

where, each of $R_4$ and $R_5$ independently represents an alkyl group having 1 to 10 carbon atoms in which each of optional and nonadjacent methylene groups may be substituted by an oxygen atom or —CH=CH—, and optional hydrogen atoms may be substituted by fluorine atoms; each of ring G, ring I and ring J independently represents trans-1,4-cyclohexylene, pyrimidine-2,5-diyl, or 1,4-phenylene in which hydrogen atoms may be substituted by fluorine atoms; each of $Z_7$ and $Z_8$ independently represents —C≡C—, —COO—, —CH$_2$CH$_2$—, —CH═CH— or a covalent bond.

12. A liquid crystal composition further containing at least one optically active compound in addition to a liquid crystal composition according to claim 6.

13. A liquid crystal element comprising a liquid crystal composition according to claim 6.

* * * * *